(12) United States Patent
Deitch et al.

(10) Patent No.: US 9,615,904 B2
(45) Date of Patent: Apr. 11, 2017

(54) SACROCOLPOPEXY SUPPORT

(71) Applicant: Coloplast A/S, Humlebaek (DK)

(72) Inventors: Sarah J. Deitch, Minneapolis, MN (US); Randy Lee Morningstar, Brooklyn Park, MN (US); Mark A. Moschel, New Hope, MN (US); Michael M. Witzmann, Shoreview, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 14/295,356

(22) Filed: Jun. 4, 2014

(65) Prior Publication Data

US 2014/0343355 A1    Nov. 20, 2014

Related U.S. Application Data

(63) Continuation of application No. 13/013,823, filed on Jan. 26, 2011, now abandoned, which is a (Continued)

(30) Foreign Application Priority Data

Jun. 3, 2010   (DK) ................................. 2010 70241

(51) Int. Cl.
*A61F 2/02*   (2006.01)
*A61F 2/00*   (2006.01)
(Continued)

(52) U.S. Cl.
CPC ........ *A61F 2/0045* (2013.01); *A61B 17/0401* (2013.01); *A61B 17/06109* (2013.01);
(Continued)

(58) Field of Classification Search
CPC ... A61F 2/0045; A61F 2002/0817–2002/0841; A61F 2002/0852;
(Continued)

(56) References Cited

U.S. PATENT DOCUMENTS 6,117,067 A   9/2000   Gil-Vernet
6,221,005 B1  4/2001   Bruckner et al.
(Continued)

FOREIGN PATENT DOCUMENTS

AU   2002241673   8/2002
DE   19544162     11/1997
(Continued)

OTHER PUBLICATIONS

Bard Nordic, Ajust TM Adjustable Single-Incision Sling, URL "http:/www.bardnordic.com/main/product.asp?sectionTypeid=2 &sectionid=6&productid=296" accessed Mar. 2, 2009.

*Primary Examiner* — Catherine B Kuhlman
(74) *Attorney, Agent, or Firm* — Coloplast Corp., Coloplast A/S; Nick Baumann

(57) ABSTRACT

A sacrocolpopexy support includes a Y-shaped body having a planar base and a pair of legs extending from the planar base, a first interconnecting member coupled to the planar base of the Y-shaped body, and an adjustable anchor coupled to and movable bi-directionally along the first interconnecting member.

13 Claims, 34 Drawing Sheets

Related U.S. Application Data continuation of application No. 12/793,682, filed on Jun. 4, 2010, now Pat. No. 8,720,446, application No. 14/295,356, which is a continuation-in-part of application No. 14/181,607, filed on Feb. 14, 2014, which is a continuation of application No. 12/717,957, filed on Mar. 5, 2010, now Pat. No. 8,696,544, which is a continuation-in-part of application No. 12/621,517, filed on Nov. 19, 2009, now Pat. No. 8,585,579, and a continuation-in-part of application No. 12/414,709, filed on Mar. 31, 2009, now Pat. No. 8,585,578.

(60) Provisional application No. 61/150,276, filed on Feb. 5, 2009.

(51) Int. Cl.
 *A61B 17/04* (2006.01)
 *A61B 17/06* (2006.01)
 *A61B 17/00* (2006.01)

(52) U.S. Cl.
 CPC ............ *A61B 2017/00805* (2013.01); *A61B 2017/045* (2013.01); *A61B 2017/0409* (2013.01); *A61B 2017/0414* (2013.01); *A61B 2017/0427* (2013.01); *A61B 2017/0448* (2013.01); *A61B 2017/0464* (2013.01); *A61B 2017/0496* (2013.01)

(58) Field of Classification Search
 CPC .. A61B 2017/00805; A61B 2017/0446; A61B 2017/045; A61B 2017/0451
 See application file for complete search history.

(56) References Cited

U.S. PATENT DOCUMENTS

| | | | |
|---|---|---|---|
| 6,406,420 B1* | 6/2002 | McCarthy et al. | ............. 600/16 |
| 6,527,794 B1* | 3/2003 | McDevitt | ........... A61B 17/0401 |
| | | | 606/1 |
| 6,592,515 B2 | 7/2003 | Thierfelder et al. | |
| 6,660,023 B2 | 12/2003 | McDevitt et al. | |
| 6,695,855 B1 | 2/2004 | Gaston | |
| 6,960,160 B2 | 11/2005 | Browning | |
| 7,083,568 B2 | 8/2006 | Neisz et al. | |
| 7,094,199 B2 | 8/2006 | Petros et al. | |
| D534,650 S | 1/2007 | Inman et al. | |
| 7,175,591 B2 | 2/2007 | Kaladelfos | |
| 7,204,802 B2 | 4/2007 | DeLeval | |
| 7,223,229 B2 | 5/2007 | Inman et al. | |
| 7,288,063 B2 | 10/2007 | Petros et al. | |
| 7,291,104 B2 | 11/2007 | Neisz et al. | |
| 7,347,812 B2 | 3/2008 | Mellier | |
| 7,410,460 B2 | 8/2008 | Benderev | |
| 7,422,557 B2 | 9/2008 | Arnal et al. | |
| 7,837,710 B2 | 11/2010 | Lombardo et al. | |
| 7,901,346 B2 | 3/2011 | Kovac et al. | |
| 7,985,173 B2 | 7/2011 | Jacquetin | |
| 8,585,578 B2 | 11/2013 | Morningstar et al. | |
| 8,585,579 B2 | 11/2013 | Moschel et al. | |
| 8,608,643 B2 | 12/2013 | Morningstar et al. | |
| 8,696,544 B2 | 4/2014 | Deegan et al. | |
| 8,720,446 B2 | 5/2014 | Deitch | |
| 2002/0028980 A1* | 3/2002 | Thierfelder et al. | ............. 600/37 |
| 2003/0130670 A1 | 7/2003 | Anderson et al. | |
| 2003/0199729 A1 | 10/2003 | Grise | |
| 2003/0220538 A1 | 11/2003 | Jacquetin | |
| 2003/0229361 A1* | 12/2003 | Jackson | ............. A61B 17/0487 |
| | | | 606/144 |
| 2004/0039453 A1 | 2/2004 | Anderson et al. | |
| 2004/0138706 A1 | 7/2004 | Abrams et al. | |
| 2005/0004576 A1 | 1/2005 | Benderev | |
| 2005/0021086 A1 | 1/2005 | De Leval | |
| 2005/0055052 A1* | 3/2005 | Lombardo et al. | ........... 606/232 |
| 2005/0075660 A1 | 4/2005 | Chu et al. | |
| 2005/0277985 A1 | 12/2005 | Wert et al. | |
| 2005/0288692 A1 | 12/2005 | Beraud et al. | |
| 2006/0063968 A1 | 3/2006 | Anderson et al. | |
| 2006/0089525 A1 | 4/2006 | Mamo et al. | |
| 2006/0122457 A1 | 6/2006 | Kovac et al. | |
| 2006/0205995 A1 | 9/2006 | Browning | |
| 2006/0229493 A1 | 10/2006 | Weiser et al. | |
| 2006/0229596 A1 | 10/2006 | Weiser et al. | |
| 2006/0260618 A1 | 11/2006 | Hodroff et al. | |
| 2007/0015953 A1 | 1/2007 | MacLean | |
| 2007/0015957 A1 | 1/2007 | Li | |
| 2007/0021649 A1 | 1/2007 | Nowlin et al. | |
| 2007/0038017 A1 | 2/2007 | Chu | |
| 2007/0055095 A1 | 3/2007 | Chu et al. | |
| 2007/0225546 A1 | 9/2007 | Anderson et al. | |
| 2007/0293717 A1 | 12/2007 | Kaleta et al. | |
| 2008/0021265 A1 | 1/2008 | Garbin et al. | |
| 2008/0051836 A1 | 2/2008 | Foerster et al. | |
| 2008/0139877 A1 | 6/2008 | Chu et al. | |
| 2008/0140218 A1 | 6/2008 | Staskin et al. | |
| 2008/0196729 A1 | 8/2008 | Browning | |
| 2008/0287956 A1 | 11/2008 | Smith et al. | |
| 2008/0287968 A1 | 11/2008 | Smith et al. | |
| 2009/0023978 A1 | 1/2009 | Arnal et al. | |
| 2009/0137862 A1 | 5/2009 | Evans et al. | |
| 2009/0187067 A1 | 7/2009 | Carteron et al. | |
| 2010/0030016 A1 | 2/2010 | Knoll | |
| 2010/0063542 A1* | 3/2010 | van der Burg | ..... A61B 17/0401 |
| | | | 606/232 |
| 2010/0121349 A1* | 5/2010 | Meier | ................ A61B 17/0467 |
| | | | 606/139 |
| 2010/0198003 A1 | 8/2010 | Morningstar et al. | |
| 2010/0198004 A1 | 8/2010 | Moschel et al. | |
| 2010/0256442 A1 | 10/2010 | Ogdahl et al. | |
| 2011/0263930 A1 | 10/2011 | Rapp | |
| 2011/0301407 A1 | 12/2011 | Deitch | |
| 2012/0108894 A1* | 5/2012 | Young et al. | ................... 600/37 |

FOREIGN PATENT DOCUMENTS

| | | |
|---|---|---|
| WO | 03068107 A1 | 8/2003 |
| WO | 03096929 A1 | 11/2003 |
| WO | 2004017845 A1 | 3/2004 |
| WO | 2004017862 A2 | 3/2004 |
| WO | 2004045457 A1 | 6/2004 |
| WO | 2005122954 A1 | 12/2005 |
| WO | 2006034719 A1 | 4/2006 |
| WO | 2006045042 A1 | 4/2006 |
| WO | 2006084167 A1 | 8/2006 |
| WO | 2006108145 A1 | 10/2006 |
| WO | 2007049154 A1 | 5/2007 |
| WO | 2007059199 A2 | 5/2007 |
| WO | 2007097994 | 8/2007 |
| WO | 2007097994 A2 | 8/2007 |
| WO | 2007109759 A2 | 9/2007 |
| WO | 2007149348 A2 | 12/2007 |
| WO | 2007149555 A2 | 12/2007 |
| WO | 2007149593 A2 | 12/2007 |
| WO | 2009102945 A2 | 8/2009 |
| WO | 2010088917 | 8/2010 |
| WO | 2011082350 A1 | 7/2011 |
| WO | 2012119145 A1 | 9/2012 |

\* cited by examiner

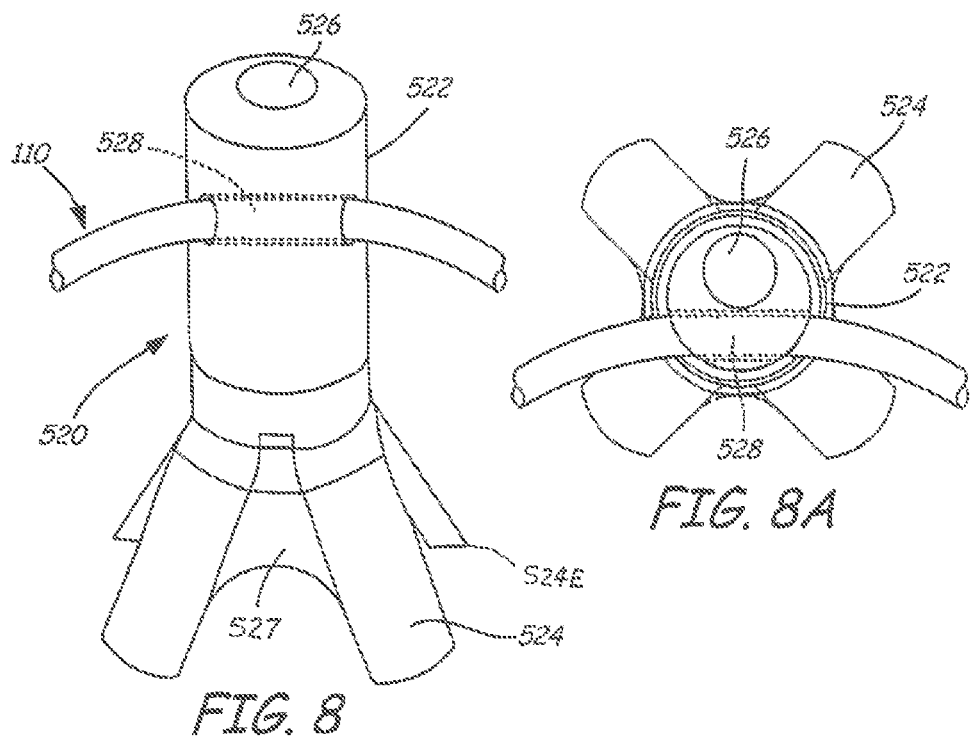
FIG. 8
FIG. 8A
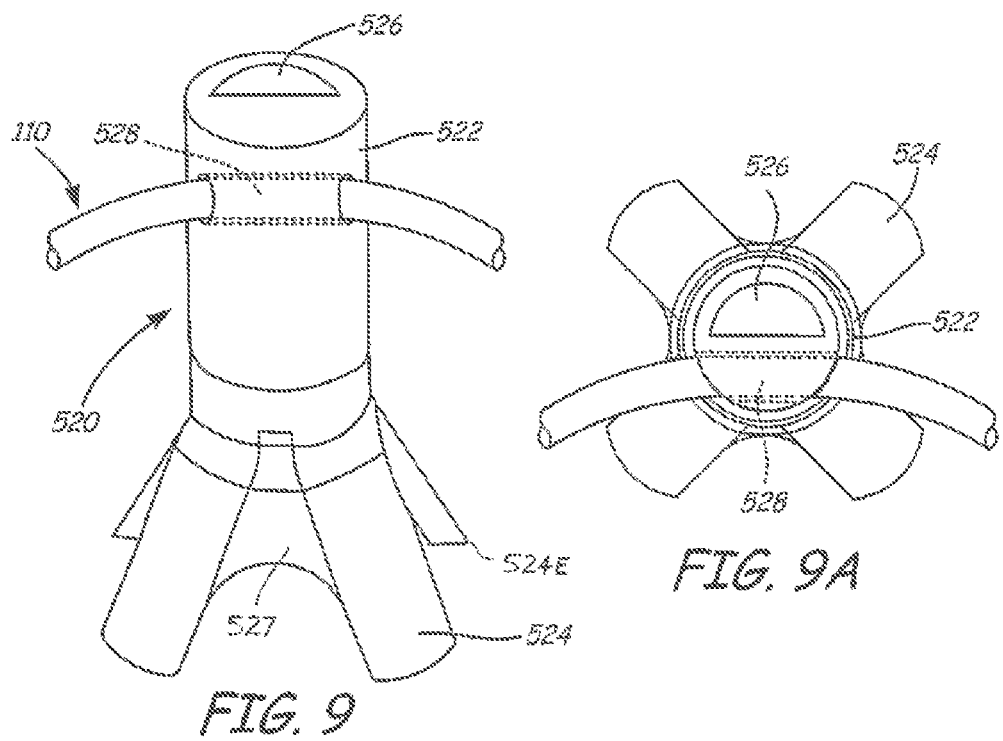
FIG. 9
FIG. 9A

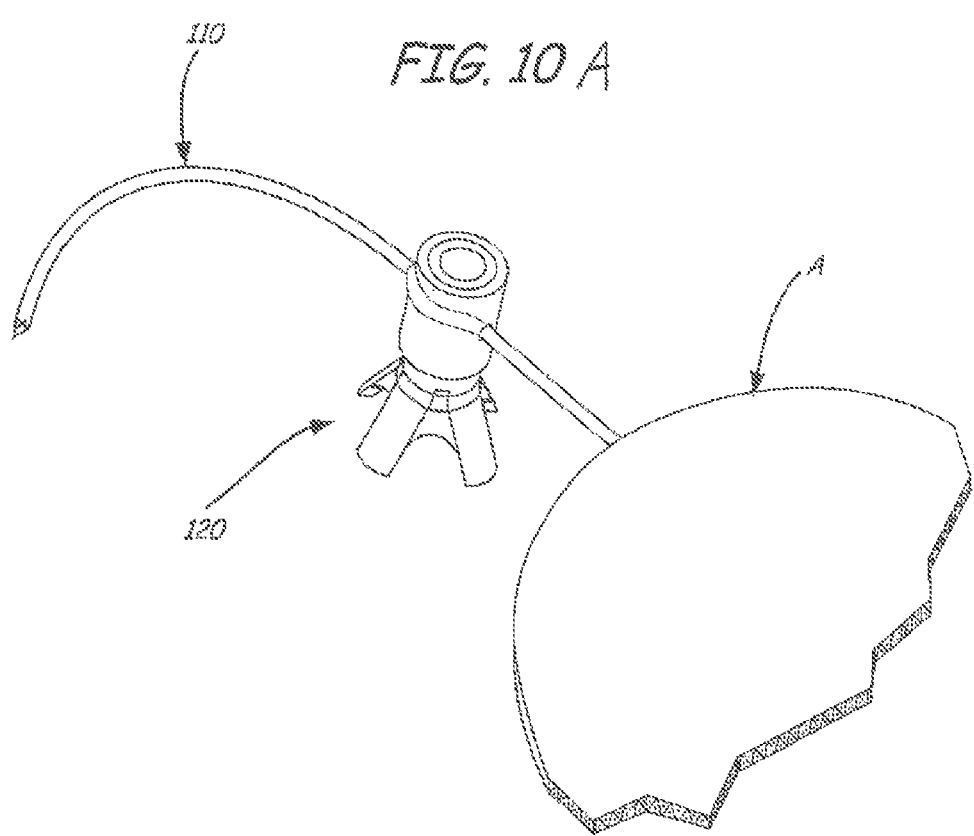

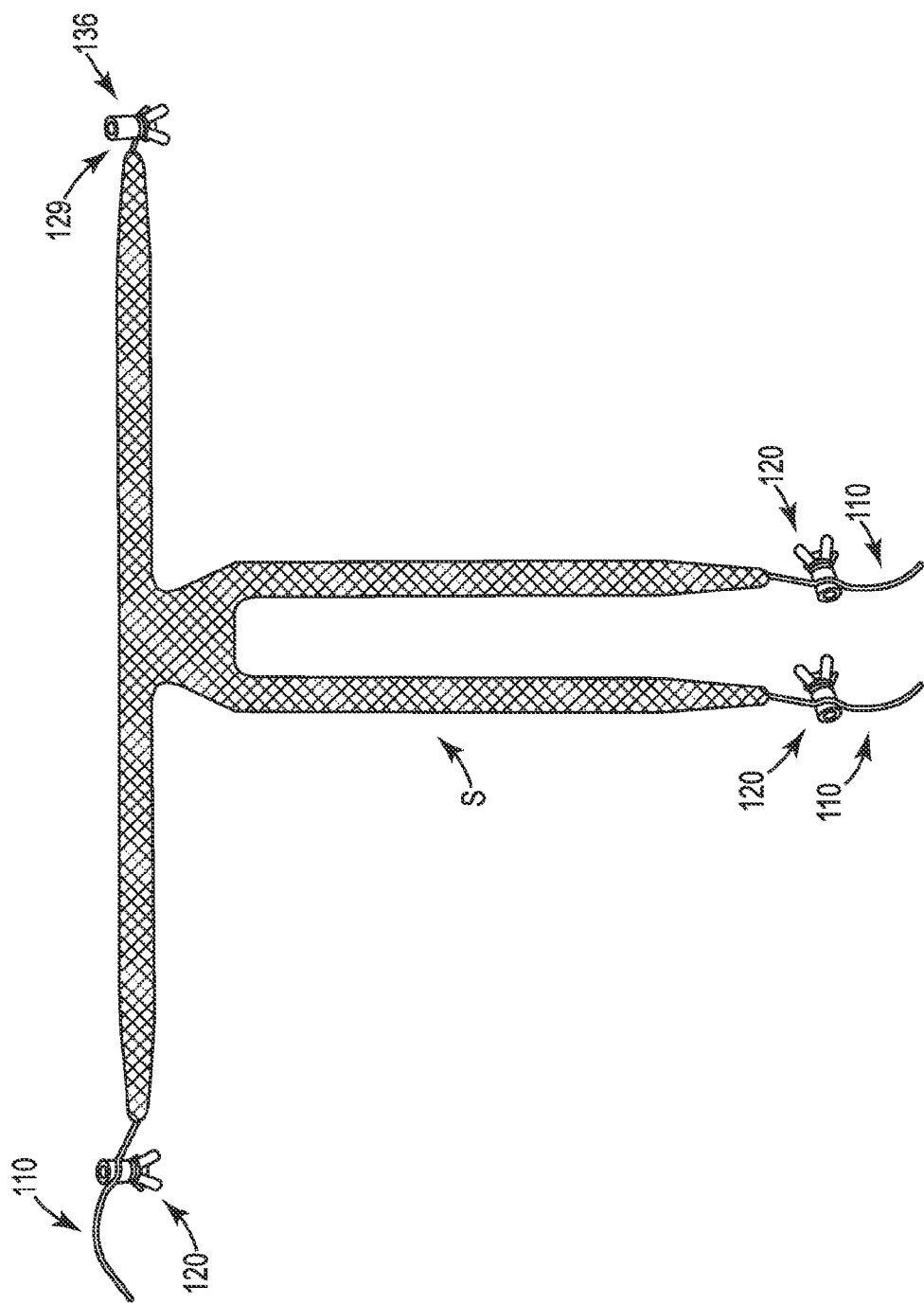

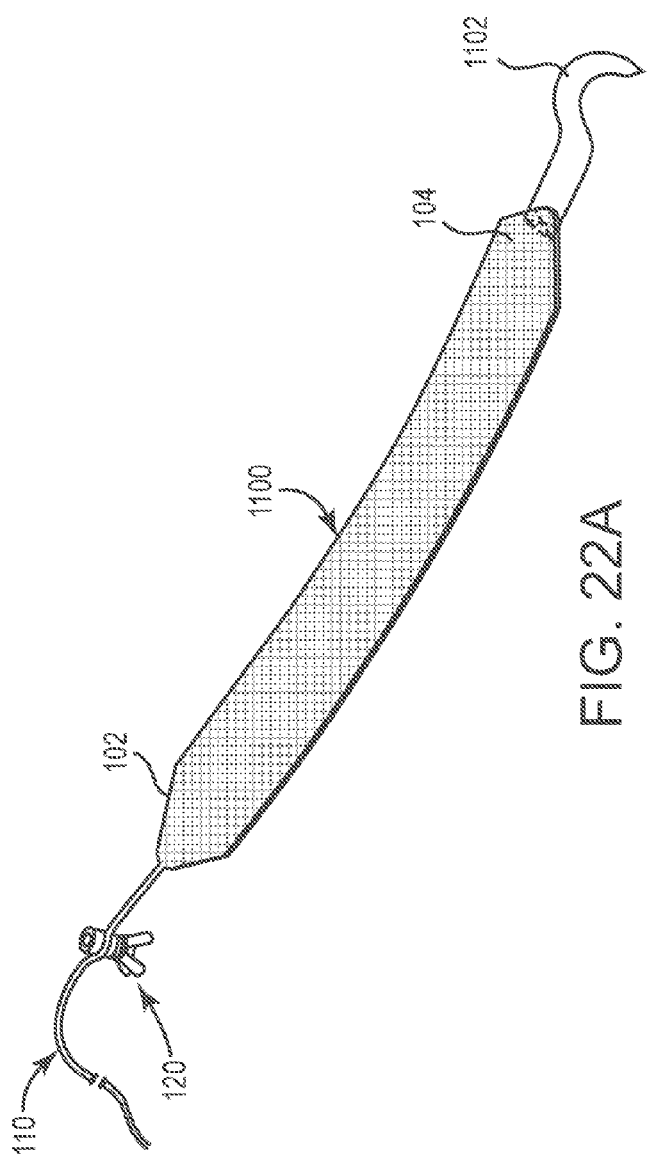
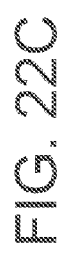
FIG. 22A
FIG. 22C
FIG. 22B

SACROCOLPOPEXY SUPPORT

BACKGROUND

Devices for anatomical support, and particularly those for treatment of urinary incontinence and pelvic organ prolapse have been proposed in recent years. Such devices have included suburethral sling devices for urinary incontinence, and mesh devices for pelvic organ prolapse. Sling devices are surgically implanted under a patient's urethra to provide support to the urethra so that during a provocative event such as coughing or laughing, urine is inhibited from leaking out of the urethra. Devices for treatment of pelvic organ prolapse are also surgically implanted, to inhibit herniation or prolapse of an organ (e.g., the bladder) into the vaginal space. Such support from the sling and mesh devices replaces natural anatomical support that is lacking in the patient. But implanting and anatomically securing some devices may be difficult and time consuming. Further, in the case of urinary incontinence, some sling devices may provide unreliable anatomical fixation and unacceptable adjustment or tensioning for supporting the urethra, thereby leading to suboptimal or even unacceptable results for treatment of urinary incontinence.

SUMMARY

This disclosure describes novel implantable devices that provide support to a urethra or other anatomical structure. This disclosure also describes novel tools and methods for use with the implantable devices.

In one aspect, an implantable device for anatomical support includes a sling, a first interconnecting member that is coupled to the sling, and a second interconnecting member that is coupled to the sling. An adjustable anchor is slidably coupled to the first interconnecting member to permit bi-directional movement along the first interconnecting member, and configured to exert a compressive force generating frictional interference between the adjustable anchor and the first interconnecting member, to inhibit the bi-directional movement of the adjustable anchor along the first interconnecting member unless sufficient force is applied to overcome the frictional interference. Also, a fixed anchor is fixedly coupled to the second interconnecting member. In another aspect, the first interconnecting member and the second interconnecting member are sutures. In another aspect, the first interconnecting member and the second interconnecting member are materials having an overall width approximating that of a surgical suture.

In another aspect, an implantable device for anatomical support includes a sling, a first interconnecting member that is coupled to the sling, and a second interconnecting member that is coupled to the sling. An anchor is provided in freely sliding engagement with the first interconnecting member. A tensioning element is slidably coupled to the first interconnecting member to permit movement along the first interconnecting member and configured to exert a compressive force generating frictional interference between the tensioning element and the first interconnecting member, to inhibit the movement of the tensioning element along the first interconnecting member unless sufficient force is applied to overcome the frictional interference. Also, a fixed anchor is fixedly coupled to the second interconnecting member. In another aspect, the first interconnecting member and the second interconnecting member are sutures. In another aspect, the first interconnecting member and the second interconnecting member are materials having an overall width approximating that of a surgical suture.

In another aspect, an implantable device for anatomical support includes an anatomical support member and an interconnecting member that is coupled to the anatomical support member. An adjustable anchor is slidably coupled to the interconnecting member to permit bi-directional movement along the interconnecting member and configured to exert a compressive force generating frictional interference between the adjustable anchor and the interconnecting member, to inhibit the bi-directional movement of the adjustable anchor along the interconnecting member unless sufficient force is applied to overcome the frictional interference. In another aspect, the anatomical support member is a shaped mesh material for treatment of prolapse. In another aspect, the interconnecting member is a suture. In another aspect, the interconnecting member is a material having an overall width approximating that of a surgical suture.

In another aspect, an implantable device for anatomical support includes an anatomical support member, an interconnecting member that is coupled to the anatomical support member, and an anchor in freely sliding engagement with the interconnecting member. A tensioning element is slidably coupled to the interconnecting member to permit movement along the interconnecting member and configured to exert a compressive force generating frictional interference between the tensioning element and the interconnecting member, to inhibit the movement of the tensioning element along the interconnecting member unless sufficient force is applied to overcome the frictional interference. In another aspect, the interconnecting member is a suture. In another aspect, the interconnecting member is a material having an overall width approximating that of a surgical suture.

In another aspect an adjustable anchor, for use with an anatomical support member having an interconnecting member extending therefrom, includes a body having a proximal end and a distal end, wherein the distal end includes a flange section that is wider than the proximal end. A collar surrounds, and generates a compressive force against, the proximal end of the body, wherein the interconnecting member is disposed between the body and the collar, subject to the compressive force that generates frictional interference to inhibit bi-directional movement of the adjustable anchor along the interconnecting member unless sufficient force is applied to overcome the frictional interference. In another aspect, a plurality of flanges protrude from the flange section, separated by webs. In another aspect, at least one flange has an angled edge. In another aspect, at least one web is self-creasing.

In another aspect an adjustable anchor and a tool, for placing in a patient an anatomical support member having an interconnecting member extending therefrom, includes an anchor body having a proximal end, a distal end, and a channel extending longitudinally through the anchor body, wherein the distal end includes a flange section that is wider than the proximal end. An anchor collar surrounds, and generates a compressive force against, the proximal end of the anchor body, wherein the interconnecting member is disposed between the anchor body and the anchor collar, subject to the compressive force that generates frictional interference to inhibit bi-directional movement of the adjustable anchor along the interconnecting member unless sufficient force is applied to overcome the frictional interference. A tool shaft has a proximal end, a shoulder, and a distal tip proximate the shoulder. A helical curve in the shaft terminates at the shoulder. The distal tip is configured to be placed in the channel through the anchor body such that the shoulder abuts the anchor body adjacent to the flange section. The helical curve is configured to guide the distal tip from a vaginal incision, around a descending ramus, and through an obturator foramen. In another aspect, a handle is coupled to the proximal end.

In another aspect a surgical method is provided for use with (i) an implantable device having an anatomical support member, a fixed anchor coupled to the implantable device, an adjustable anchor, and an interconnecting member that couples the implantable device to the adjustable anchor in frictional sliding engagement, (ii) a first tool corresponding to a first side of a patient, and (iii) a second tool corresponding to a second side of a patient. The method includes placement of the fixed anchor on a distal tip of the first tool. A vaginal incision in the patient is entered with the fixed anchor on the distal tip of the first tool. The first tool is rotated in a direction corresponding to the first side of the patient such that the fixed anchor travels in a path around a descending pubic ramus on the first side of the patient, continuing in the path until the fixed anchor is placed in obturator tissue on the first side of the patient; and the first tool is removed from the patient. An adjustable anchor is placed on a distal tip of the second tool. The vaginal incision in the patient is entered with the adjustable anchor on the distal tip of the second tool. The second tool is rotated in a direction corresponding to the second side of the patient such that the adjustable anchor travels in a path around a descending pubic ramus on the second side of the patient, continuing in the path until the adjustable anchor is placed in obturator tissue on the second side of the patient; and the second tool is removed from the patient. The interconnecting member, in frictional sliding engagement with the adjustable anchor, is pulled to adjust a length of the interconnecting member between the anatomical support member and the adjustable anchor.

In another aspect an implantable anatomical support includes a support body and at least three arms extending from the support body, an interconnecting member that is coupled to one each of at least two of the arms extending from the support body, and an adjustable anchor slidably coupled to each of at least two of the interconnecting members. The adjustable anchor is configured to permit bi-directional movement along the interconnecting member and configured to exert a compressive force generating frictional interference between the adjustable anchor and the interconnecting member to inhibit the bi-directional movement of the adjustable anchor along the interconnecting member unless sufficient force is applied to overcome the frictional interference.

Another aspect provides a method of addressing pelvic dysfunction in a patient. The method includes forming an incision, and placing an anchor that is attached to a support member by an interconnecting member onto a distal tip of a tool. The method additionally includes inserting the distal tip of the tool and the anchor into the incision, guiding the anchor to an obturator foramen, and pushing the anchor through a membrane extending over the obturator foramen. The method further includes adjusting the support member by sliding the interconnecting member relative to the anchor.

BRIEF DESCRIPTION OF THE DRAWINGS

FIG. 8 is a magnified illustration of one of the components shown in FIG. 6.

FIG. 8A is a top view of the component shown in FIG. 8.

FIG. 9 is a magnified illustration of an alternative component for the device shown in FIG. 6.

FIG. 9A is a top view of the component shown in FIG. 9.

FIG. 10A is a partial illustration of another embodiment of an implantable device for anatomical support.

FIG. 10C is an illustration of another embodiment of an implantable device for anatomical support

FIG. 22A is a perspective view of one embodiment of a support member including an adjustable anchor and a hanger.

FIG. 22B is a side view and FIG. 22C is a front view of the hanger illustrated in FIG. 22A.

DETAILED DESCRIPTION

Figure 1:
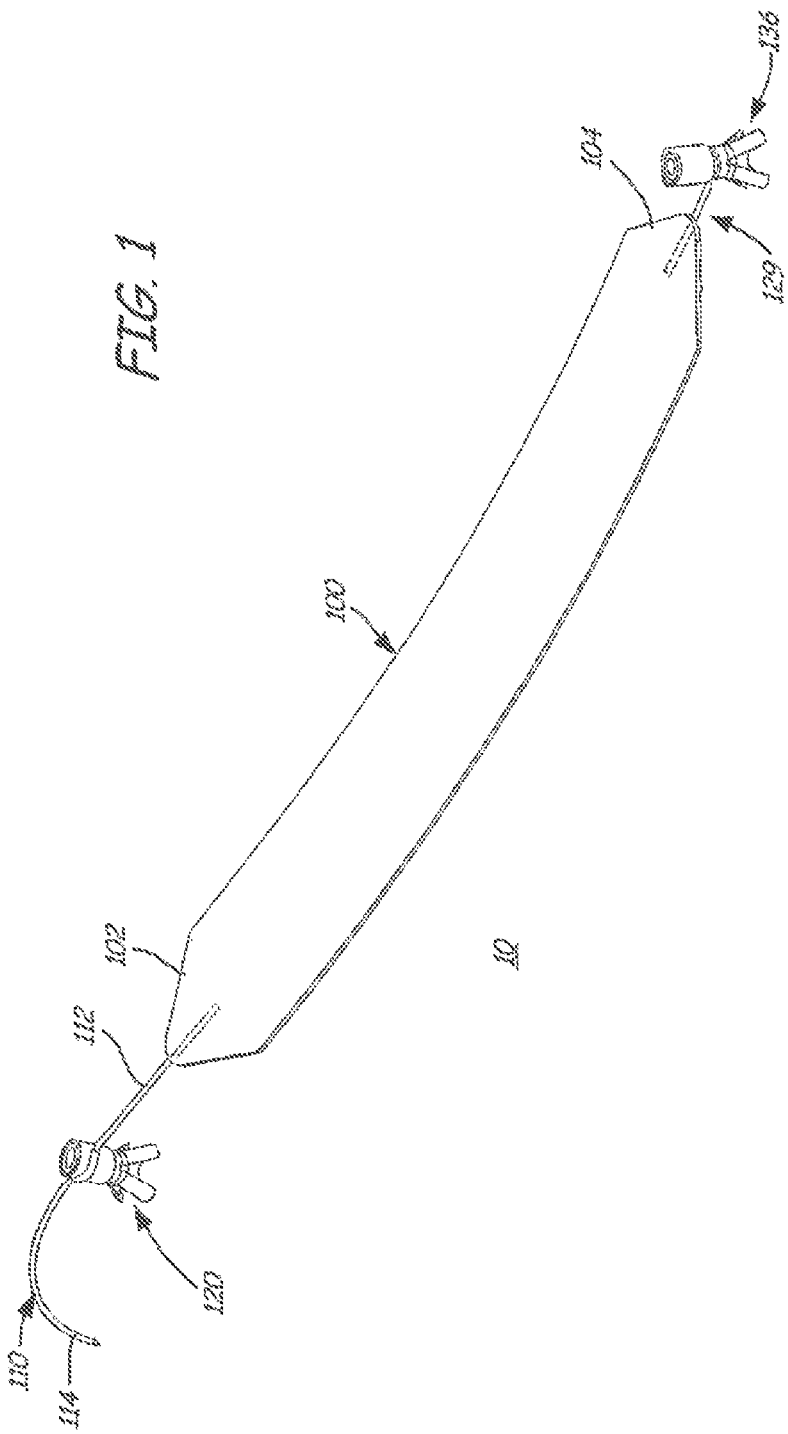
FIG. 1 is an illustration of one embodiment of an implantable device for anatomical support.

One embodiment of an implantable device for anatomical support (device 10) is illustrated in FIG. 1. Therein, an anatomical support member in a form of a suburethral sling includes anchors that are deployed into a patient's tissues. The anchors are coupled to the sling by interconnecting members. In this regard a fixed anchor is fixedly connected in fixed relation to the sling by a first interconnecting member, and an adjustable anchor is slidably coupled in adjustable relation to the sling by a second interconnecting member. The adjustable anchor, as will be described, is configured to permit bi-directional movement along the second interconnecting member in frictional sliding engagement therewith. In one embodiment, the interconnecting members are lengths of suture or suture-like material.

Figure 2:
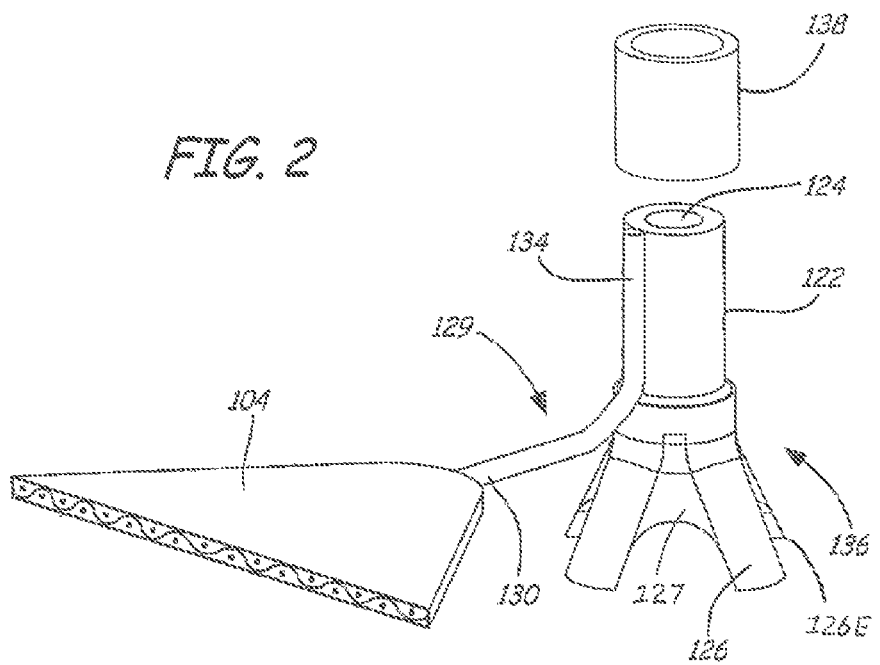
FIG. 2 is an exploded illustration of a component of the implantable device shown in FIG. 1.

With particular reference to FIGS. 1 and 2, an example of device 10 includes a suburethral sling 100 with opposing ends 102 and 104. Device 10 also includes interconnecting member 110 having opposing ends 112 and 114, and interconnecting member 129 having opposing ends 130 and 134. End 112 of interconnecting member 110 is coupled to end 102 of sling 100; and as shown in FIG. 2 end 130 of interconnecting member 129 is coupled to end 104 of sling 100. Although shown in the drawings via phantom lines as being coupled to an underside or bottom surface of sling 100, it is to be understood that the coupling of interconnecting members 110 and 129 to sling 100 may be provided at any suitable surface of sling 100 and at any suitable orientation thereon.

Also as shown in FIG. 2, in one embodiment device 10 includes a fixed anchor 136 having a body 122 with a proximal end and a distal end, and a channel 124 extending longitudinally therethrough. A plurality of flanges 126 protrude from the distal end, separated by webs 127. End 134 of interconnecting member 129 is fixedly coupled to body 122. Fixed anchor 136 also includes a collar 138. When assembled for use in device 10 as shown in FIG. 1, collar 138 covers the proximal end of body 122 of fixed anchor 136 and end 134 of interconnecting member 129 coupled to body 122.

Figure 3:
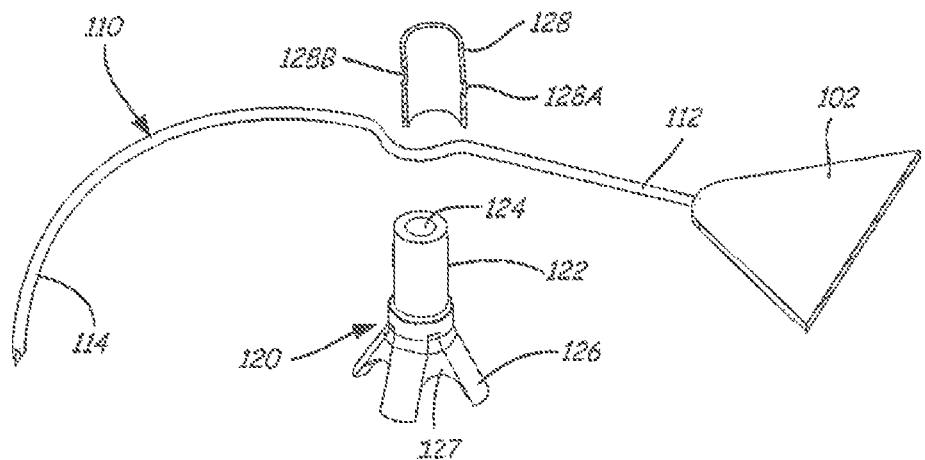
FIG. 3 is an exploded illustration of another component of the implantable device shown in FIG. 1.
Figure 4:
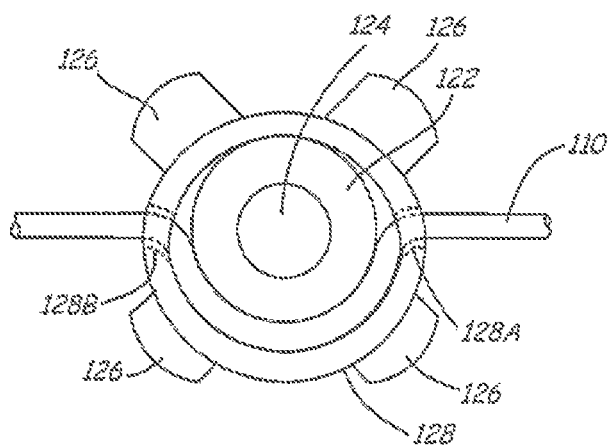
FIG. 4 is an assembled, top view of the component shown in FIG. 3.

Device 10 also includes an adjustable anchor 120. Referring to FIGS. 3 and 4, in one embodiment adjustable anchor 120 includes a body 122 having a proximal end and a distal end, with a channel 124 extending longitudinally therethrough and a plurality of flanges 126 protruding from the distal end that are in turn separated by webs 127. As shown in FIG. 3 in exploded half-section, and in a top assembly view in FIG. 4, adjustable anchor 120 has a collar 128 surrounding the proximal end that includes a pair of apertures 128A and 128B. When assembled for use in device 10, collar 128 covers body 122 of adjustable anchor 120 while apertures 128A-B in collar 128 permit passage of interconnecting member 110 therethrough in frictional sliding engagement with adjustable anchor 120. In this regard and with reference to FIG. 4, it is to be appreciated and understood that interconnecting member 110 is disposed through aperture 128A of collar 128, around a partial circumference of body 122, and through aperture 128B of collar 128. By virtue of an intentionally close fit to exert a compressive force and thus frictional interference between interconnecting member 110, collar 128, and body 122, adjustable anchor 120 is slidably coupled to interconnecting member 110 to permit bi-directional movement along interconnecting member 110 upon overcoming such frictional interference.

It is to be understood that an amount of compressive force and thus desired frictional interference could be varied among embodiments of adjustable anchor 120 with regard to an elasticity of a particular material chosen for collar 128 and also with regard to placement of apertures 128A and 128B in collar 128. For example, with locations of apertures 128A-B being constant, if a material chosen for collar 128 in a first embodiment of adjustable anchor 120 has less elasticity than a material chosen for collar 128 in a second embodiment of adjustable anchor 120, then the compressive force and resulting frictional interference of the first embodiment would be greater than that of the second embodiment due to, comparatively, greater resistance of collar 128 against interconnecting member 110 in the first embodiment than in the second embodiment. Similarly, with a material for collar 128 being constant, if apertures 128A-B are placed farther apart in one embodiment of anchor 120 than in a second embodiment of anchor 120, then the compressive force and resulting frictional interference of the first embodiment would be greater than that of the second embodiment due to, comparatively, a longer path through adjustable anchor 120 of interconnecting member 110 in the first embodiment than in the second embodiment.

Figure 5:
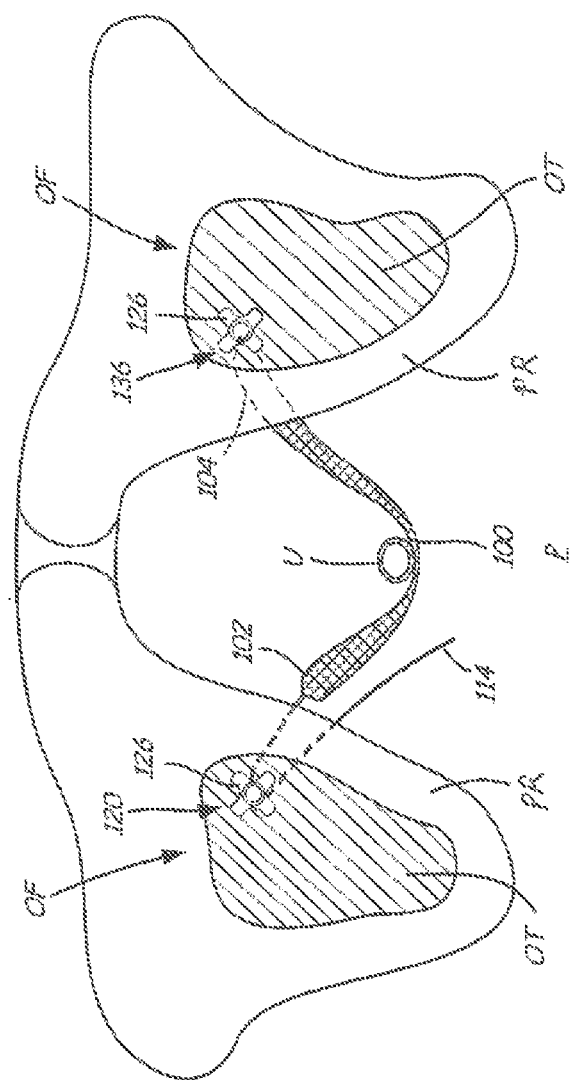
FIG. 5 is an illustration of the implantable device shown in FIG. 1, after implantation in a patient.

This feature of frictional sliding engagement between interconnecting member 110 and adjustable anchor 120 enables adjustment and tensioning of sling 100 when implanted in a patient. Referring to FIG. 5, one embodiment of device 10 is illustrated as having been implanted in a pelvic region P of a patient that includes urethra U and obturator tissue OT in each obturator foramen OF. In the drawing suburethral sling 100 of device 10 is shown as having been positioned under the patient's urethra U, with placement of fixed anchor 136 in obturator tissue OT of one obturator foramen OF and placement of adjustable anchor 120 in obturator tissue OT in the other obturator foramen OF. If desired, positions of anchors 120 and 136 could be exchanged in a left and right sense relative to pelvic region P. As will be further described, flanges 126 and webs 127 of anchors 120 and 136 secure the placement of each anchor in respective obturator tissue OT; and in one embodiment, at least one flange 126 has an angled or beveled edge 126E to promote such secure placement in obturator tissue OT or other anatomical tissue.

In one embodiment, at least one web 127 is self-creasing. Specifically, upon application of pressure to flange 126 such as when anchors 120 and 136 are being deployed through and secured at selected anatomical tissue, web 127 tends to fold or crease which thereby tends to facilitate, advantageously, a temporary bending or deflection of an adjacent flange 126 downwardly and inwardly toward longitudinal channel 124. In turn, this downward or inward bending or deflection of flange 126 tends to facilitate such deployment of the anchor through and into the tissue. Furthermore, upon such deployment through tissue, web 127 advantageously tends to inhibit an inverse bending or deflection of flange 126 upwardly toward body 122.

By way of the coupling of interconnecting members 110 and 129 to anchors 120 and 136 respectively, and the coupling of interconnecting members 110 and 129 to ends 102 and 104 of sling 100 respectively, sling 100 is maintained in position as desired under urethra U. With fixed anchor 136 and adjustable anchor 120 so implanted in obturator tissue OT, and with regard to the frictional sliding engagement between interconnecting member 110 and adjustable anchor 120, it is to be particularly understood that pulling on end 114 of interconnecting member 110 away from adjustable anchor 120 with a force sufficient to overcome the aforementioned interference force between interconnecting member 110 and adjustable anchor 120 would cause interconnecting member 110 to pass through anchor 120 with a resultant shortening of a distance between end 102 of sling 100 and adjustable anchor 120. Thereby, sling 100 would be raised or elevated under urethra U as may be desired and as will be further described. Conversely, pulling on end 112 of interconnecting member 110 away from adjustable anchor 120 (or pulling on sling 100 away from anchor 120, or so pulling on both end 112 and sling 100) with such force would overcome the interference and cause interconnecting member 110 to pass in an opposite direction through anchor 120 with a resultant lengthening of a distance between end 102 of sling 100 and adjustable anchor 120. Thereby, sling 100 would be lowered under urethra U as may be desired and as will be further described.

It is to be appreciated and understood that the novel construction and operation of device 10 is to be provided with respect to three force parameters. First, device 10 is to be constructed such that adjustable anchor 120 is not destroyed or otherwise damaged upon frictional sliding movement of interconnecting member 110 through anchor 120. Second, device 10 is to be constructed such that neither fixed anchor 136 nor, particularly, adjustable anchor 120 are pulled out or dislodged from obturator tissue OT into which they have been placed and secured, upon movement of interconnecting member 110 through adjustable anchor 120 during intraoperative adjustment. Third, device 10 is to be constructed such that the aforementioned interference force between interconnecting member 110 and adjustable anchor 120 is sufficiently high to inhibit movement of sling 100 under urethra U during a provocative event such as coughing by the patient when internal anatomical forces are exerted upon device 10.

In one embodiment, sling 100 has a length of about 7 cm (2.76 in.) and a width in a range of about of 8 mm (0.315 in.) to 11 mm (0.433 in.). Further, in one embodiment sling 100 is a medical grade material such as, for example, knitted polypropylene ARIS® brand mesh material that is commercially available from Coloplast A/S; and interconnecting members 110 and 129 are lengths of medical grade suture or suture-like materials as aforementioned. In another embodiment, interconnecting members 110 and 129 could be, for example, the aforementioned polypropylene material of sling 100 that has been knitted, woven, or otherwise formed into an elongated suture-like filamentary material. In another embodiment interconnecting members 110 and 129 could be, variously alone or together, continuations of the material of sling 100 configured to have characteristics of a suture-like filamentary material. Accordingly, such embodiments would provide a material having an overall width approximating that of a surgical suture.

Anchors 120 and 136 could be manufactured using any suitable materials such as polypropylene and polyurethane, and fabrication techniques such as molding and milling. In one embodiment, body 122, flanges 126, and webs 127 are fabricated from polypropylene. In one embodiment, collar 128 is molded from a thermoplastic polyurethane material or polymeric elastomer such as TECOTHANE® brand material. In one embodiment, anchors 120 and 136 have an overall length of 0.622 cm (0.245 in.) and a maximum width at flanges 126 of 0.470 cm (0.185 in.). In one embodiment, flanges 126 have a width of 0.114 cm (0.045 in.) and a thickness of 0.038 cm (0.015 in.). In one embodiment, webs 127 have a thickness of approximately one-half that of flanges 126, or about 0.019 cm (0.008 in.). In one embodiment, body 122 has a length of 0.312 cm (0.123 in.) and a diameter of 0.172 cm (0.068 in.). In one embodiment, longitudinal channel 124 in body 122 has a diameter of 0.097 cm (0.038 in.). In one embodiment, before being assembled as described below, collar 128 has an inner diameter of 0.127 cm (0.050 in.), an outer diameter of 0.254 cm (0.100 in.), and a length of 0.318 cm (0.125 in.); and apertures 128A-B have a diameter of 0.051 cm (0.020 in.). In one embodiment, collar 138 of anchor 136 has an inner diameter of 0.191 cm (0.075 in.), an outer diameter of 0.254 cm (0.100 in.), and a length of 0.254 cm (0.100 in.).

In one example of construction of device 10, with reference again to FIG. 2, end 112 of interconnecting member 110 is sonically welded to end 102 of sling 100; and end 134 of interconnecting member 129 is sonically welded to end 104 of sling 100. Further in this example, end 134 of interconnecting member 129 is placed against body 122 of anchor 136, and collar 138 is placed over body 122 and end 134. Those assembled components are then sonically welded, thereby securing interconnecting member 129 to anchor 136.

Regarding assembly of adjustable anchor 120, in one embodiment collar 128 is swelled by using a suitable solvent such as methylethylketone (or MEK; also referred to as butanone). Collar 128, manufactured from the thermoplastic polyurethane material as aforementioned, is immersed in the MEK for approximately four hours whereupon it swells or becomes enlarged due to infiltration of the MEK into a molecular composition of the polyurethane material causing its expansion in all dimensions. Swelled collar 128 is then loosely placed over body 122 of adjustable anchor 120, and as aforementioned end 114 of interconnecting member 110 is then passed through aperture 128A of collar 128, around a partial circumference of body 122, and through aperture 128B such that a segment of interconnecting member 110 is within apertures 128A-B. In another embodiment interconnecting member 110 is placed through apertures 128A and 128B of swelled collar 128 such that a segment of interconnecting member 110 is within apertures 128A-B, and then collar 128 is placed over body 122 of adjustable anchor 120.

That assembly is then raised to a temperature of 30 C for approximately 24 hours, to accelerate evaporation of the MEK from the thermoplastic polyurethane material. When the MEK evaporates, the swelling of collar 128 decreases, effectively returning collar 128 to its pre-swelled dimensions. Thereby, collar 128 tightly surrounds body 122 and interconnecting member 110 disposed therebetween. A result of such assembly is that interconnecting member 110 is movable through apertures 128A-B of collar 128, in frictional sliding contact between body 122 and an inside surface of collar 128.

Although a path through apertures 128A-B is illustrated as being perpendicular to longitudinal channel 124, one aperture 128A or 128B could be at a higher or lower point on collar 128 than the other aperture and thus the path through apertures 128A-B could be at another angle relative to channel 124.

Also, it is to be understood that the aforedescribed connections of components by sonic welding could instead be accomplished by any other suitable means such as, for example, by use of a suitable adhesive material.

In another embodiment, anchor 136 could be coupled directly to anatomical support member 100. In such an embodiment, interconnecting member 129 could be omitted and end 104 could be, for example, sonically welded, glued, or otherwise mechanically coupled to anchor 136 between an outside surface of body 122 and an inside surface of collar 128. In another embodiment, collar 128 could be omitted with, simply, connection of end 104 to body 122.

Figure 6:
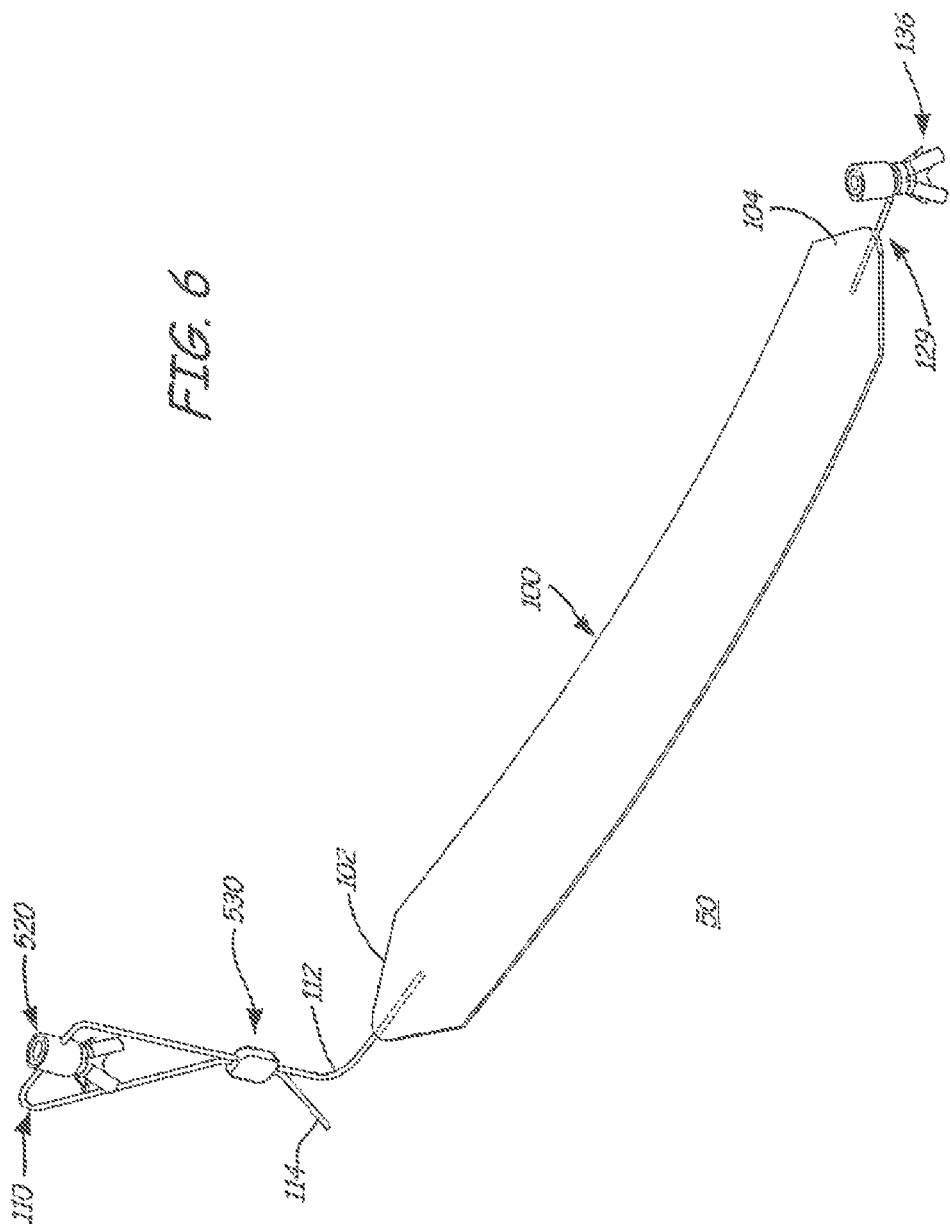
FIG. 6 is an illustration of another embodiment of an implantable device for anatomical support.

Illustrated in FIG. 6 is another example of an implantable device for anatomical support (device 50). In the drawings, like reference numerals denote like components among embodiments. Example device 50 includes an anatomical support member as a suburethral sling 100 with ends 102 and 104; interconnecting member 110 with ends 112 and 114; and interconnecting member 129 with ends 130 and 134. End 112 of interconnecting member 110 is coupled to end 102 of sling 100; and end 130 of interconnecting member 129 is fixedly coupled to end 104 of sling 100. Although shown in the drawings via phantom lines as being coupled to an underside or bottom surface of sling 100, it is to be understood that the coupling of interconnecting members 110 and 129 to sling 100 may be provided at any suitable surface of sling 100 and at any suitable orientation thereon.

Fixed anchor 136 includes a body 122 having a proximal end and a distal end, with a longitudinal channel 124 extending therethrough. A plurality of flanges 126 protruding from the distal end of body 122, separated by webs 127. End 134 of interconnecting member 129 is fixedly coupled to body 122 of fixed anchor 136; and fixed anchor 136 includes a collar 138. Collar 138 covers the proximal end of body 122 and end 134 of interconnecting member 129 coupled to body 122.

Figure 7:
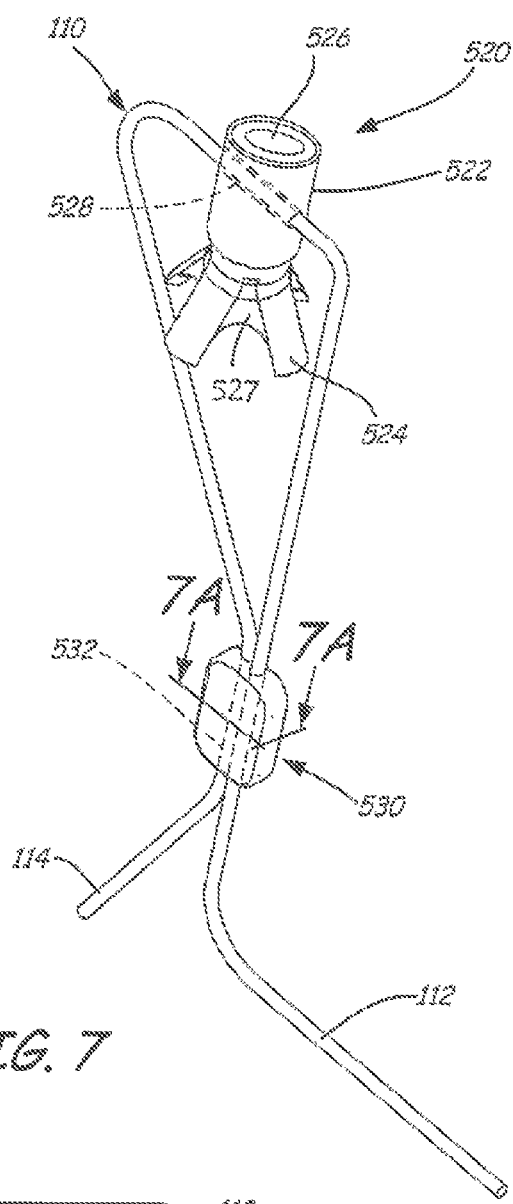
FIG. 7 is a magnified illustration of components of the implantable device shown in FIG. 6.

Referring to FIGS. 7, 8 and 8A, device 50 also includes an anchor 520 and a separate tensioning element 530 slidably coupled to interconnecting member 110. In one embodiment, anchor 520 includes a body 522 having a channel 526 extending longitudinally therethrough, and a plurality of flanges 524 protruding therefrom separated by webs 527; and in one embodiment, at least one flange 524 has an angled or beveled edge 524E to promote secure placement in obturator tissue OT or other anatomical tissue.

In one embodiment, at least one web 527 is self-creasing. Specifically, upon application of pressure to flange 524 such as when anchor 520 is being deployed through and secured at selected anatomical tissue, web 527 tends to fold or crease which thereby tends to facilitate, advantageously, a temporary bending or deflection of an adjacent flange 524 downwardly and inwardly toward longitudinal channel 526. In turn, this downward or inward bending or deflection of flange 524 tends to facilitate such deployment of the anchor through and into the tissue. Furthermore, upon such deployment through tissue, web 527 advantageously tends to inhibit an inverse bending or deflection of flange 524 upwardly toward body 522.

Figure 7A:
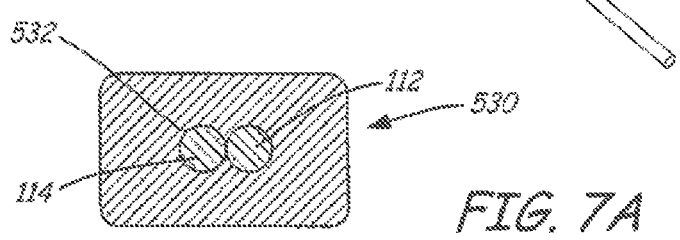
FIG. 7A is a cross-sectional view of components shown in FIG. 7, taken along lines 7A-7A.

Anchor 520 also has a channel 528 through body 522 to permit interconnecting member 110 to move therethrough in freely sliding engagement with anchor 520. In this example of device 50, and referring to FIGS. 6, 7, and 7A, interconnecting member 110 is partially disposed within tensioning element 530. In one embodiment, tensioning element 530 is fabricated from a suitable biocompatible material such as, e.g., silicone or a low durometer thermoplastic material like polyurethane. In assembly of device 50, ends 112 and 114 of interconnecting member 110 are disposed within tensioning element 530 (indicated by paths 532 in FIG. 7). In particular, although not illustrated, it is to be understood that in one embodiment end 114 of interconnecting member 110 is driven through tensioning element 530 by use of, e.g., a needle. End 114 is then placed through channel 528 of anchor 520 and then driven by the needle back through tensioning element 530. As shown in FIG. 7A, by virtue of exertion of a compressive force and thus frictional interference between tensioning element 530 and interconnecting member 110, tensioning element 530 is slidably coupled to interconnecting member 110 to permit bi-directional movement along interconnecting member 110 upon overcoming such frictional interference. This feature of sliding frictional interference between interconnecting member 110 and tensioning element 530 permits adjustment and tensioning of sling 100 when implanted in a patient. With reference to FIG. 5, it is to be understood that device 50 could be substituted for device 10 and implanted in a pelvic region P of a patient that includes urethra U and obturator tissue OT in each obturator foramen OF. Thus, suburethral sling 100 of device 50 could be positioned under the patient's urethra U, with secure placement of fixed anchor 136 in obturator tissue OT of one obturator foramen OF and by secure placement of anchor 520 in obturator tissue OT in the other obturator foramen OF. Positions of anchors 520 and 136 could be exchanged in a left and right sense relative to pelvic region P. By grasping tensioning element 530 and pulling on end 114 away from tensioning element 530 with a force sufficient to overcome the aforementioned frictional interference force between interconnecting member 110 and tensioning element 530, interconnecting member 110 slides through tensioning element 530 and thus through anchor 520 with a resultant shortening of a distance between end 102 of sling 100 and tensioning element 530. Thereby, sling 100 would be raised or elevated under urethra U. Conversely, grasping tensioning element 530 and pulling on end 112 of interconnecting member 110 away from tensioning element 530 (or pulling on sling 100 away from tensioning element 530, or so pulling on both end 112 and sling 100) with such force would overcome the interference and cause interconnecting member 110 to pass through tensioning element 530 and thus in an opposite direction through tensioning element 530 with a resultant lengthening of a distance between end 102 of sling 100 and tensioning element 530. Thereby, sling 100 would be lowered under urethra U.

Like device 10, it is to be appreciated and understood that the novel construction and operation of device 50 is to be provided with respect to three force parameters. First, device 50 is to be constructed such that tensioning element 530 is not destroyed or otherwise damaged upon frictional sliding movement of interconnecting member 110 through it. Second, device 50 is to be constructed such that neither anchor 136 nor anchor 520 are pulled out or dislodged from obturator tissue OT into which they have been placed and secured, upon of movement of interconnecting member 110 through tensioning element 530 during intraoperative adjustment. Third, device 50 is to be constructed such that the aforementioned interference force between interconnecting member 110 and tensioning element 530 is sufficiently high to inhibit movement of sling 100 under urethra U during a provocative event when the patient's internal anatomical structures or tissues exert forces upon device 50.

In one embodiment of device 50, components of anchor 520 could be constructed in dimensions, and from materials and techniques, as variously described regarding similar components of fixed anchor 136 in device 10. Furthermore, components of one embodiment of device 50 could be coupled and secured as described relative to similar components of device 10.

Another embodiment of anchor 520 is depicted in FIGS. 9 and 9A wherein channel 526 is a generally semi-circular or "D" shape. D-shaped channel 526, extending longitudinally through body 522, could provide more clearance for channel 528 compared to the longitudinal and fully cylindrical channel 526 shown in FIGS. 7, 8 and 8A. Furthermore, and although not illustrated, longitudinal channel 526 could also be provided in a smaller diameter than as shown in FIGS. 8A and 9A to thereby provide even greater clearance for channel 528. A path through channel 528 is illustrated as being perpendicular to longitudinal channel 526; but in another embodiment, the path could be at another angle relative to channel 526.

It is to be appreciated that when implanted in a patient, sling 100 of devices 10 and 50 advantageously extends nearly from obturator tissue OT on one side of the patient to obturator tissue OT on an opposite side of the patient as a result of, e.g., an intentionally short segment of interconnecting member 129 that couples end 104 of sling 100 to fixed anchor 136 and a selected length of sling 100 with respect to a typical distance between opposing obturator foramen OF.

Referring to FIG. 10A, and with additional reference to FIGS. 1, 3, and 4, it is to be appreciated that the novel adjustable anchor 120 described herein could be useful for secure placement of virtually any anatomical support member (A) coupled to an interconnecting member 110 where it is desired to provide adjustment or tensioning of the support member when implanted in a patient. Anatomical support member (A) could be, for example, a shaped mesh material for treatment of prolapse. Also, an anatomical support member could employ any number of adjustable anchors 120, with or without any number of fixed anchors 136.

Figure 10B:
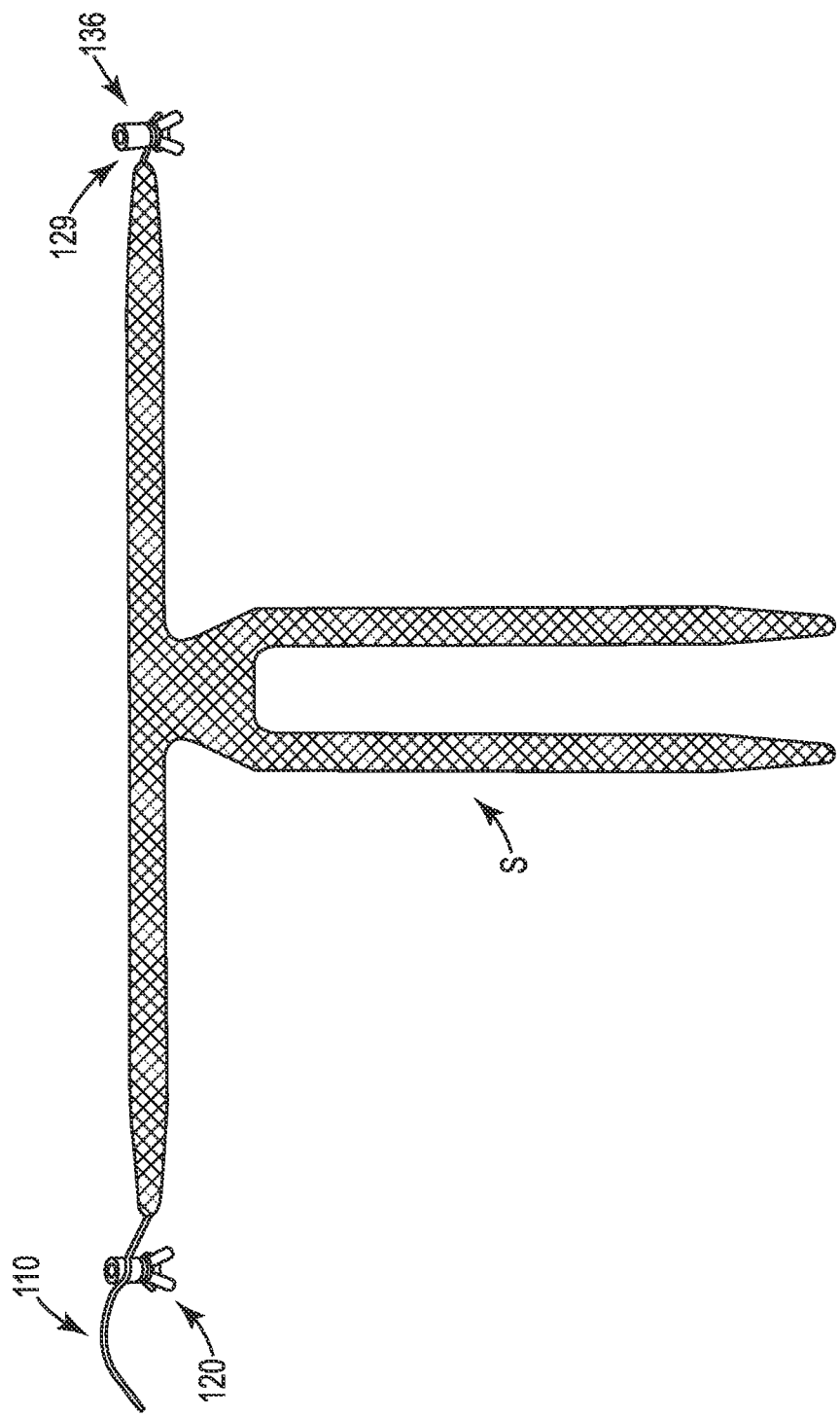
FIG. 10B is an illustration of another embodiment of an implantable device for anatomical support.

Referring to FIGS. 10B and 10C, it is to be also appreciated that the novel adjustable anchor 120 described herein could be useful with an implantable device (S) for treatment of urinary incontinence where it is desired to provide adjustment or tensioning of device (S) when implanted in a patient. Although not specifically depicted in FIGS. 10B-C, it is to be understood however that device (S) could employ any number of adjustable anchors 120, with or without any number of fixed anchors 136.

Although not illustrated in FIGS. 10A-C, it is to be understood that anchor 520 with tensioning element 530 could be utilized with any anatomical support member (A); and any number of combinations of anchor 520 with tensioning element 530 could also be utilized with or without any number of fixed anchors 136.

Regardless of a particular embodiment of adjustable anchor 120, or of anchor 520 with tensioning element 530, it is to be understood and appreciated that such novel anchors described herein may be relatively small when compared to known anatomical anchors. This advantage results from the fact that the novel anchors described herein are coupled to anatomical support members by sutures or suture-like filaments, rather than directly to the anatomical support members themselves which are usually larger and wider than sutures or suture-like filaments as in some known anatomical anchors. In alternative embodiments, any of the anchors (e.g., anchors 120, 136, or 520) would include at least one flange 126.

Figure 11:
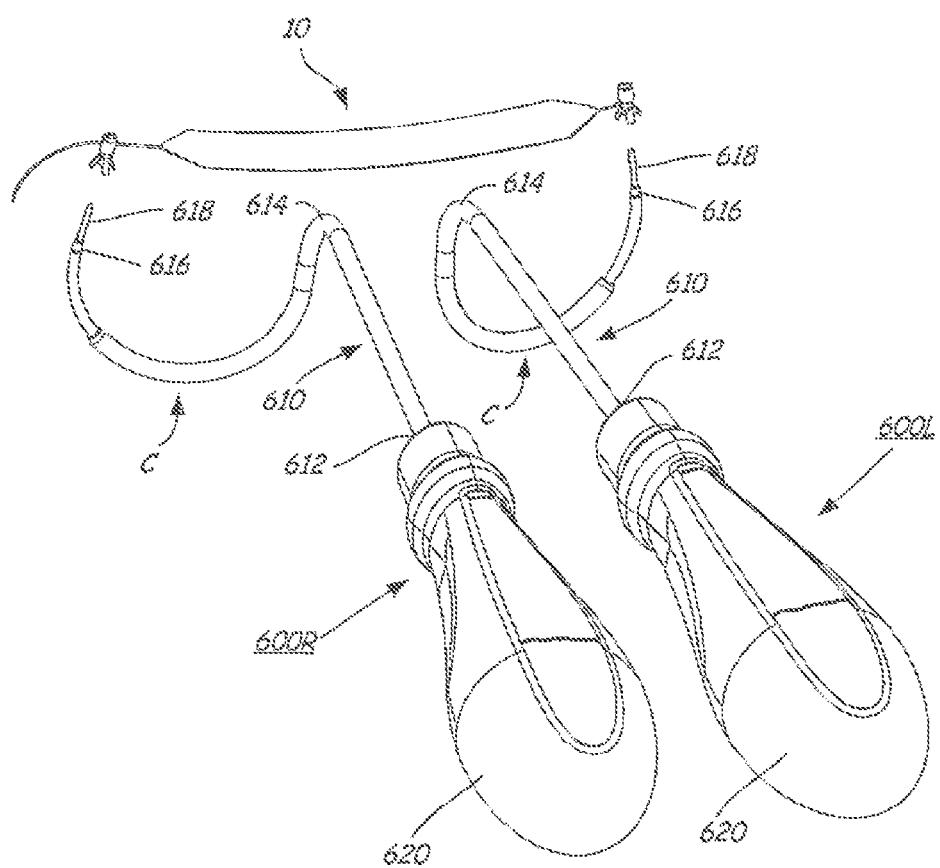
FIG. 11 is an illustration of one embodiment of a pair of tools for use in a surgical method to place an anatomical support member in a patient.
Figure 12:
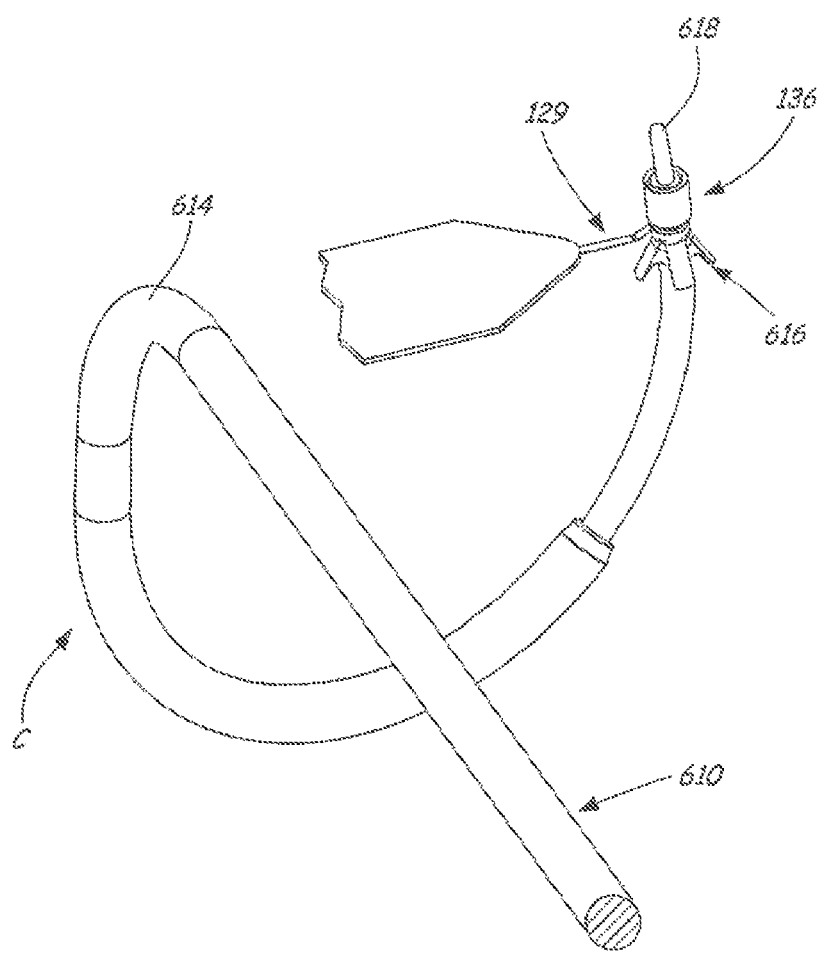
FIG. 12 is a magnified, partial illustration of one of the tools shown in FIG. 11, coupled to a component shown in FIG. 1.

FIGS. 11 and 12 illustrate an example of a tool for use in placing an implantable device for anatomical support in a patient, such as sling 100 of FIG. 1. In the drawing, a pair of tools 600R and 600L are illustrated, in left hand and right hand embodiments—with such designations referring to a patient's left and right sides, respectively. It is to be understood that the tools are identical except for a direction of a helical curve C as described below.

In this example, tools 600R and 600L each include a shaft 610 having a proximal end 612 and a cylindrical distal tip 618. A handle 620 is coupled to proximal end 612 of shaft 610. Handle 620 could have any desired shape or configuration with respect to ergonomic and other considerations of interest. A generally helical curve C is provided in shaft 610. Helical curve C terminates in a shoulder 616 proximate to distal tip 618. In use as described below, helical curve C is advantageously configured to guide tip 618 from an incision (e.g., a vaginal incision in a female patient or a perineal incision in a male patient), around a descending ramus, and through an obturator foramen OF in the patient. In this example, and as shown in FIG. 12, cylindrical distal tip 618 is configured to be placed through cylindrical channels 124 of adjustable anchor 120 and fixed anchor 136 (as shown in, e.g., in FIGS. 2 and 3), and through cylindrical channel 526 of anchor 520 (as shown, e.g., in FIGS. 7, 8, and 8A). When so placed, shoulder 616 abuts the anchor's body adjacent to the flanges with the anchor being thereby carried on tip 618 of tool 600R or 600L. Although not illustrated, it is to be understood that if an anchor was constructed with a semi-circular or "D" shaped channel 526 as depicted in FIGS. 9 and 9A, tip 618 would then be a complementary semi-circular or "D" shaped configuration.

In one embodiment, handle 620 has a length of 11.43 cm (4.5 in.). A length of shaft 610, from handle 620 to a beginning point 614 of curve C is 17.78 cm (7.0 in.). Shaft 610 has a diameter of 3 mm (0.12 in.) decreasing to 1 mm (0.04 in.) at shoulder portion 616. Curve C has a radius of curvature in a range of 2.03 cm (0.80 in.) to 2.54 cm (1.0 in.). Suitable materials for construction of handle 620 include, for example, a medical grade thermoplastic or thermoset material, preferably having both high and low durometer regions for ergonomic considerations. A suitable material for construction of shaft 610 is, for example, medical grade stainless steel. Furthermore, the tool described herein—such as the examples of tools 600R and 600L—could be disposable or sterilizable and reusable.

It is to be appreciated that in one embodiment, as shown particularly in FIG. 12, a length of distal tip 618 is chosen so that it protrudes from an anchor seated on shoulder 616. When constructed from stainless steel as aforementioned, relatively stiff tip 618 is thereby configured to pierce anatomical tissue when in use as described below. Thereby, the anchor itself does not need to include such a tissue-penetrating tip.

Referring in particular to FIGS. 1, 5, 11, and 12, an example of a surgical method to implant a device for anatomical support 10, in a form of suburethral sling 100 for treatment of urinary incontinence in a female patient, is as follows.

A catheter is placed in the patient's urethra U, among other usual and preliminary steps in preparation for surgery. The patient is placed on an operating table in a slightly exaggerated lithotomy position with buttocks extending just beyond an edge of the table. With the patient under anesthesia, a vaginal incision and blunt dissection are made. In one embodiment of the method, a fixed anchor is first placed in obturator tissue OT on the patient's left side, followed by placement of an adjustable anchor in obturator tissue OT on the patient's right side. Accordingly in this embodiment, fixed anchor 136 is placed on distal tip 618 of left hand tool 600L having an orientation of helical curve C corresponding to the patient's left side. Tip 618 of left hand tool 600L, with fixed anchor 136 seated thereupon, is placed within the vaginal incision. Left hand tool 600L is then rotated such that rotation of helical curve C advances tip 618 and fixed anchor 136 in a path around a descending pubic ramus (PR) on the patient's left side, continuing in that path until fixed anchor 136 penetrates obturator tissue OT on the patient's left side (as may be indicated by an audible or tactile "pop") and is thus secured therein. By virtue of flanges 126, fixed anchor 136 is inhibited from being pulled back through obturator tissue OT so penetrated as shown in FIG. 5. Left hand tool 600L is then removed from the patient. Next in this embodiment, adjustable anchor 120 is placed on distal tip 618 of right hand tool 600R having an orientation of helical curve C corresponding to the patient's right side. Tip 618 of right hand tool 600R, with adjustable anchor 120 seated thereupon, is placed within the vaginal incision. Right hand tool 600R is then rotated such that rotation of helical curve C advances tip 618 and adjustable anchor 120 in a path around a descending pubic ramus (PR) on the patient's right side, continuing in that path until adjustable anchor 120 penetrates obturator tissue OT on the patient's right side (as may be indicated by an audible or tactile "pop") and is thus secured therein. By virtue of flanges 126, adjustable anchor 120 is inhibited from being pulled back through obturator tissue OT so penetrated as shown in FIG. 5. Right hand tool 600R is then removed from the patient.

With suburethral sling 100 thus placed and secured in the patient by way of fixed anchor 136 and adjustable anchor 120, an assessment is made of whether sling 100 is unacceptably loose or tight under urethra U. If sling 100 is unacceptably loose, then end 114 of interconnecting member 110 is pulled away from adjustable anchor 120 with a force sufficient to overcome the aforementioned interference force between interconnecting member 110 and adjustable anchor 120. Interconnecting member 110 thus passes through anchor 120 with a resultant shortening of a distance between end 102 of sling 100 and adjustable anchor 120. Thereby sling 100 is raised or elevated under urethra U as desired. Conversely, if sling 100 is unacceptably tight, then end 112 of interconnecting member 110 is pulled away from adjustable anchor 120 (or sling 100 is pulled away from adjustable anchor 120, or both end 112 and sling 100 are so pulled) with a force sufficient to overcome the interference force between interconnecting member 110 and adjustable anchor 120. Interconnecting member 110 thus passes through anchor 120 with a resultant lengthening of a distance between end 102 of sling 100 and adjustable anchor 120. Thereby sling 100 is lowered under urethra U as desired. These steps of shortening and lengthening a distance between end 102 of sling 100 and adjustable anchor 120 may be repeated in any order and as frequently as necessary to provide optimal suburethral support from sling 100 to urethra U. The vaginal incision is then closed and usual post-operative procedures are performed.

In another embodiment, the aforedescribed method could employ an example of device 50 as shown in FIGS. 6-8A. In this embodiment of the method, a catheter is placed in the patient's urethra U and the aforementioned preliminary steps in preparation for surgery are performed. The patient is placed in a slightly exaggerated lithotomy position with buttocks extending just beyond an edge of an operating table; and under anesthesia, a vaginal incision and blunt dissection are made in the patient. In one embodiment of this method using device 50, a fixed anchor is first placed in obturator tissue OT on the patient's left side, followed by placement of an anchor in obturator tissue OT on the patient's right side that is associated with a separate tensioning element. Accordingly, fixed anchor 136 is placed on distal tip 618 of left hand tool 600L having an orientation of helical curve C corresponding to the patient's left side. Tip 618 of left hand tool 600L, with fixed anchor 136 seated thereupon, is placed within the vaginal incision. Left hand tool 600L is then rotated such that rotation of helical curve C advances tip 618 and fixed anchor 136 in a path around a descending pubic ramus (PR) on the patient's left side, continuing in that path until fixed anchor 136 penetrates obturator tissue OT on the patient's left side (as may be indicated by an audible or tactile "pop") and is thus secured therein. By virtue of flanges 126, fixed anchor 136 is inhibited from being pulled back through obturator tissue OT so penetrated as shown in FIG. 5. Left hand tool 600L is then removed from the patient. Next in this embodiment using device 50, anchor 520 is placed on distal tip 618 of right hand tool 600R having an orientation of helical curve C corresponding to the patient's right side. Tip 618 of right hand tool 600R, with anchor 520 seated thereupon, is placed within the vaginal incision. Right hand tool 600R is then rotated such that rotation of helical curve C advances tip 618 and anchor 520 in a path around a descending pubic ramus (PR) on the patient's right side, continuing in that path until anchor 520 penetrates obturator tissue OT on the patient's right side (as may be indicated by an audible or tactile "pop") and is thus secured therein. By virtue of flanges 126, anchor 520 is inhibited from being pulled back through obturator tissue OT so penetrated. Right hand tool 600R is then removed from the patient.

With suburethral sling 100 of device 50 thus placed and secured in the patient by way of fixed anchor 136 and anchor 520, an assessment is made of whether sling 100 is unacceptably loose or tight under urethra U. If sling 100 is unacceptably loose, then tensioning element 530 is grasped and end 114 of interconnecting member 110 is pulled away from tensioning element 530 with a force sufficient to overcome the aforementioned interference force between interconnecting member 110 and tensioning element 530. Interconnecting member 110 thus passes through anchor 520 with a resultant shortening of a distance between end 102 of sling 100 and tensioning element 530. Thereby sling 100 is raised or elevated under urethra U as desired. Conversely, if sling 100 is unacceptably tight, then tensioning element 530 is grasped and end 112 of interconnecting member 110 is pulled away from tensioning element 530 (or sling 100 is pulled away from tensioning element 530, or both end 112 and sling 100 are so pulled) with a force sufficient to overcome the interference force between interconnecting member 110 and tensioning element 530. Interconnecting member 110 thus passes through anchor 120 with a resultant lengthening of a distance between end 102 of sling 100 and tensioning element 530. Thereby sling 100 is lowered under urethra U as desired. Similarly to device 10, these steps of shortening and lengthening a distance between end 102 of sling 100 and tensioning element 530 in device 50 may be repeated in any order and as frequently as necessary to provide optimal suburethral support from sling 100 to urethra U. The vaginal incision is then closed and usual post-operative procedures are performed.

The adjustable anchor 120 and/or the fixed anchor 136 are each suited for attachment to support devices having a variety of shapes, including the rectangular shapes described and illustrated above, non-rectangular shapes described and illustrated below, or other symmetrical or non-symmetrical shapes as appropriate for providing anatomical support.

Figure 13:
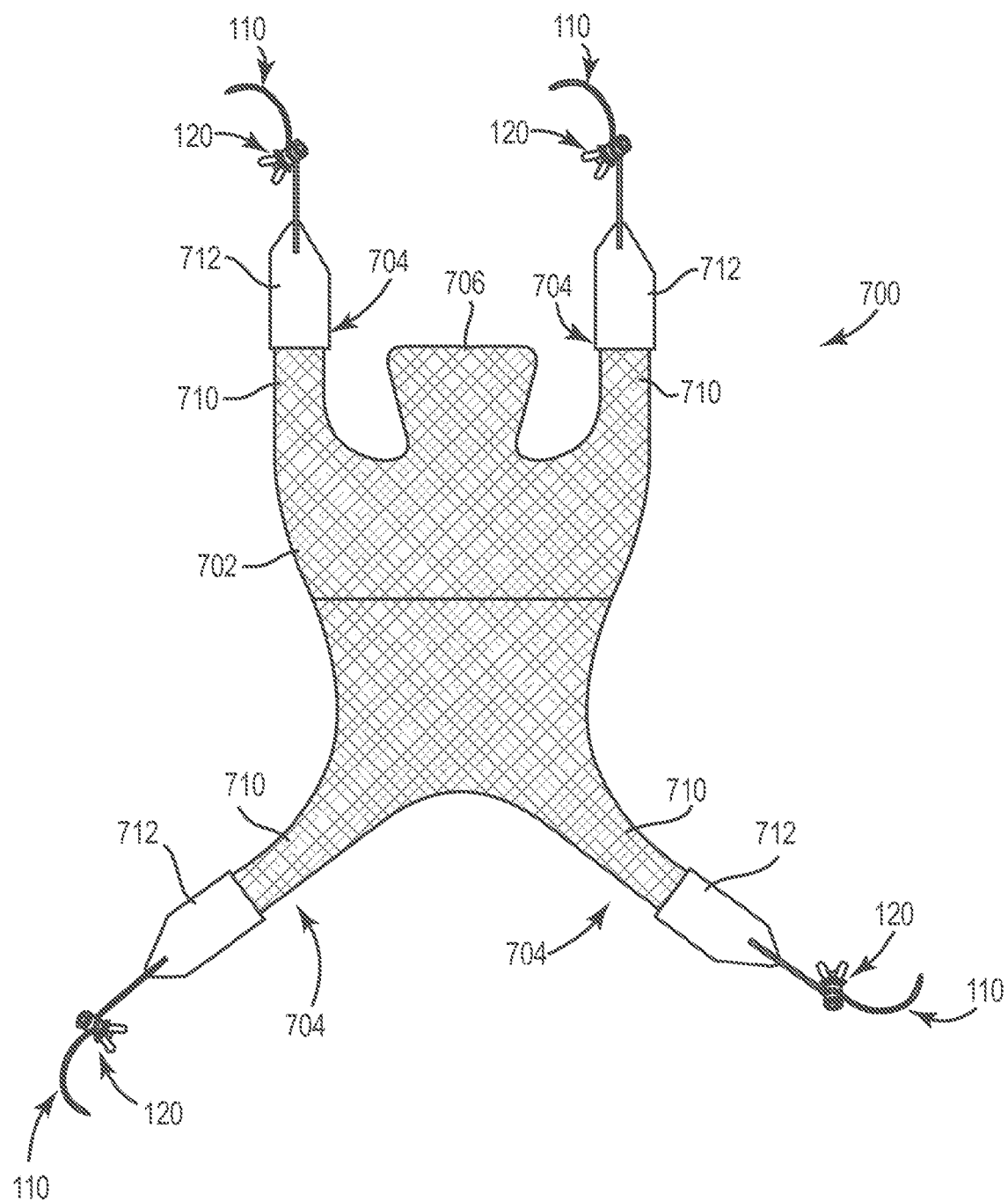
FIG. 13 is a top view of one embodiment of an implantable anatomical support device.

FIG. 13 is a top view of one embodiment of an implantable anatomical support 700 device. The implantable anatomical support 700 includes a support body 702 with at least three arms 704 extending from the support body 702, an interconnecting member 110 that is coupled to each of the arms 704 extending from the support body 702, and an adjustable anchor 120 slidably coupled to each of at least two of the interconnecting members 110.

The adjustable anchors 120 are configured for bi-directional movement along the interconnecting member 110 and exert a compressive force generating frictional interference between the adjustable anchor 120 and the interconnecting member 110. The frictional interference between the adjustable anchor 120 and the interconnecting member 110 inhibits the bi-directional movement of the adjustable anchor 120 along the interconnecting member 110 unless sufficient force is applied to overcome the frictional interference.

The arms 704 in combination with the interconnecting members 110 and the adjustable anchors 120 allow the anatomical support 700 to be implanted in a body and adjusted into a desired tensioned position. The interconnecting members 110 and the adjustable anchors 120 obviate the use of multiple skin exit punctures, and eliminate the use of retriever components and sleeves around the arms 704 that are at times employed with support bodies having arms.

The support body 702 is non-rectangular and the support 700 includes four arms 704 extending from the non-rectangular support body 702. In one embodiment, the support body 702 has a curved outside perimeter with bilateral symmetry relative to a central longitudinal axis of the non-rectangular support body 702. In one embodiment, the support body 702 has four arms 704 and includes a central tail 706 located between two of the arms 704. The central tail is configured for attachment to a suitable pelvic landmark, such as a ligament or other tissue. In one embodiment, the support body 702 is fabricated from a porous mesh configured to be compatible with biological in-situ tissue ingrowth.

In one embodiment, the arms 704 include a first arm segment 710 extending from support body 702 and a second arm segment 712 extending from the first arm segment 710, where the interconnecting members 110 extend from the second arm segment 712.

In one embodiment, the second arm segment 712 is the removed end portion 104 of the sling 100 described above and is attached to body 702. In one embodiment, the second arm segment 712 is fabricated from the knitted polypropylene material described above and is attached to the first arm segment 710 and the support body 702. In one embodiment, the first arm segment 710 is fabricated from a different material than the second arm segment 712. Suitable attachment methods for attaching the second arm segment 712 to the first arm segment 710 include adhesive attachment, mechanical attachment devices such as clips, and energetic attachments such as sonic or ultrasonic welds, as examples.

In one embodiment, the first arm segment 710 is fabricated from the same material as the second arm segment 712. For example, each of the first arm segment 710 and the second arm segment 712 is fabricated from knitted polypropylene ARIS® brand mesh material that is commercially available from Coloplast A/S.

In one embodiment, the first arm segments 710 extend 1 cm or more from the support body 702. In one embodiment, one or more of the first arm segments 710 is provided as a "stubby" arm segment that extends from the support body 702 by less than 1 cm, for example. The second arm segment 712 extends from the first arm segment 710 (whether of the "stubby" format or not). The interconnecting member 110 is attached to the second arm segment 712, and one or the other of the adjustable anchor 120 or the fixed anchor 136 is attached to the interconnecting member 110.

In one embodiment, an interconnecting member 110 is attached to each arm 704 and an adjustable anchor 120 is attached to each interconnecting member 110. In one embodiment, an interconnecting member 110 is attached to each arm 704 and a fixed anchor 136 (FIG. 1) is attached to at least one of the interconnecting members 110. It will be recognized that the implantable anatomical support 700 could include one or more adjustable anchors with anywhere from zero to one or more fixed anchors. It is to be appreciated, then, that the device 700 could employ any number of adjustable anchors 120, with or without any number of fixed anchors 136.

Figure 14:
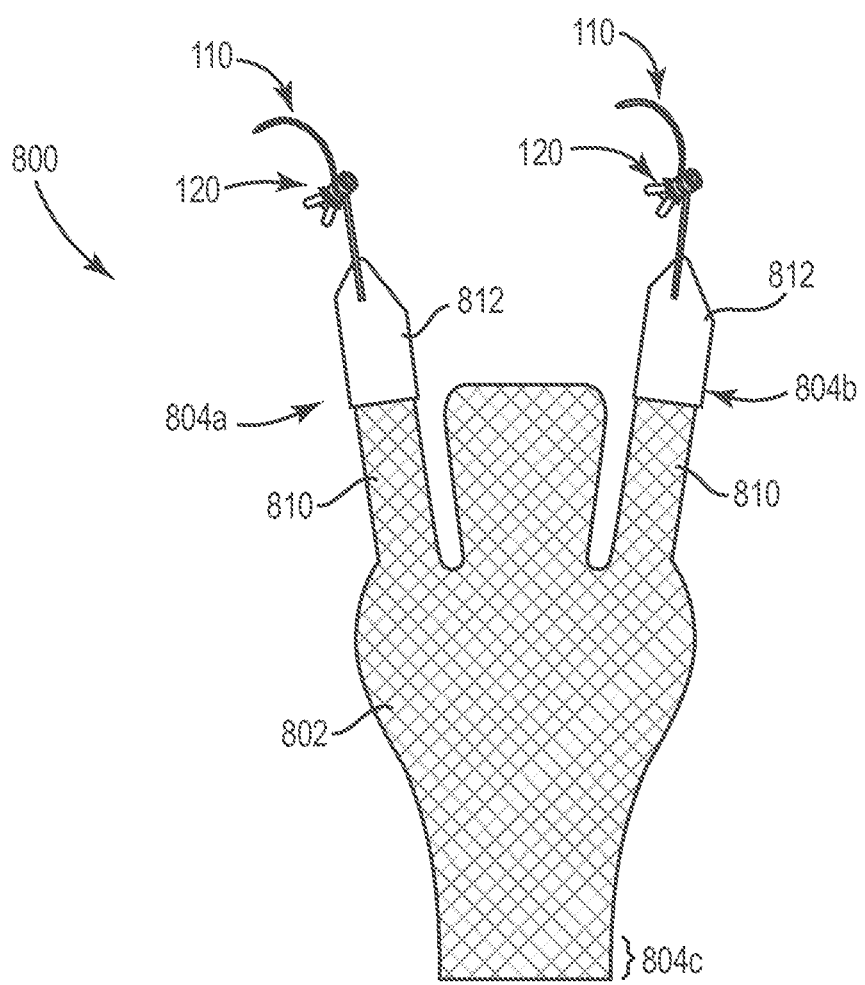
FIG. 14 is a top view of one embodiment of an implantable anatomical support device.

FIG. 14 is a top view of one embodiment of an implantable anatomical support 800. The implantable anatomical support 800 includes a support body 802 with at least three arms 804 extending from the support body 802, an interconnecting member 110 that is coupled to the arms 804 extending from the support body 802, and an adjustable anchor 120 slidably coupled to each of at least two of the interconnecting members 110.

The adjustable anchors 120 are configured for bi-directional movement along the interconnecting member 110 and exert a compressive force generating frictional interference between the adjustable anchor 120 and the interconnecting member 110. The frictional interference between the adjustable anchor 120 and the interconnecting member 110 inhibits the bi-directional movement of the adjustable anchor 120 along the interconnecting member 110 unless sufficient force is applied to overcome the frictional interference.

The arms 804 in combination with the interconnecting members 110 and the adjustable anchors 120 allow the anatomical support 800 to be implanted in a body and adjusted into a desired tensioned position. The interconnecting members 110 and the adjustable anchors 120 obviate the use of multiple skin exit puncture, and eliminate the use of retriever components and sleeves around the arms 804 that are at times employed with support bodies having arms.

The support body 802 is non-rectangular and the support 800 includes two arms 804a, 804b extending from one side of the non-rectangular support body 802 and a third arm 804c that is provided opposite the two arms 804a, 804b. In one embodiment, the support body 802 has a curved outside perimeter with bilateral symmetry relative to a central longitudinal axis of the non-rectangular support body 802.

In one embodiment, the support body 802 has three arms 804, with an interconnecting member 110 attached to one each of the two arms 804a, 804b with the third arm 804c configured for direct attachment to body tissue, for example via sutures. In one embodiment, the support body 802 is fabricated from a porous mesh configured to be compatible with biological in-situ tissue ingrowth.

In one embodiment, the arms 804a, 804b are provided with a first arm segment 810 extending from support body 802 and a second arm segment 812 extending from the first arm segment 810, where the interconnecting members 110 extend from the second arm segment 812.

Figure 15:
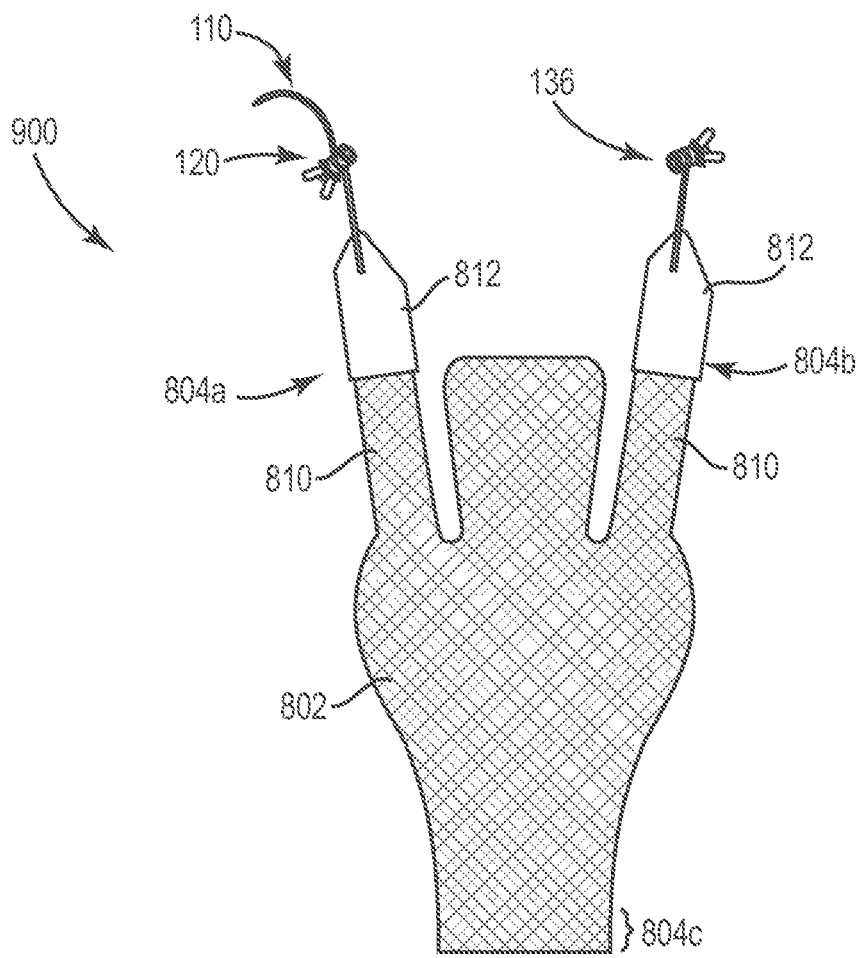
FIG. 15 is a top view of one embodiment of an implantable anatomical support device.

FIG. 15 is a top view of one embodiment of an implantable anatomical support 900. The implantable anatomical support 900 is similar to the implantable anatomical support 800 and includes the support body 802 with the arms 804 extending from the support body 802, with one adjustable anchor 120 slidably coupled to one interconnecting member 110 and a fixed anchor 136 connected to another interconnecting members 110. During implantation, the surgeon selectively attaches the fixed anchor 136 to appropriately identified tissue, attaches the adjustable anchor to adjacent tissue, and adjusts the adjustable anchor 120 along the interconnection member 110 to suitably adjust the tension in the support 900.

Although not illustrated in FIGS. 13-14, it is to be understood that anchor 520 with tensioning element 530 (FIG. 6) could be utilized with anatomical support 700 and any number of combinations of anchor 520 with tensioning element 530 could also be utilized with or without any number of fixed anchors 136.

It is to be understood that the features of the various exemplary embodiments described herein may be combined with each other, unless specifically noted otherwise.

Figure 16:
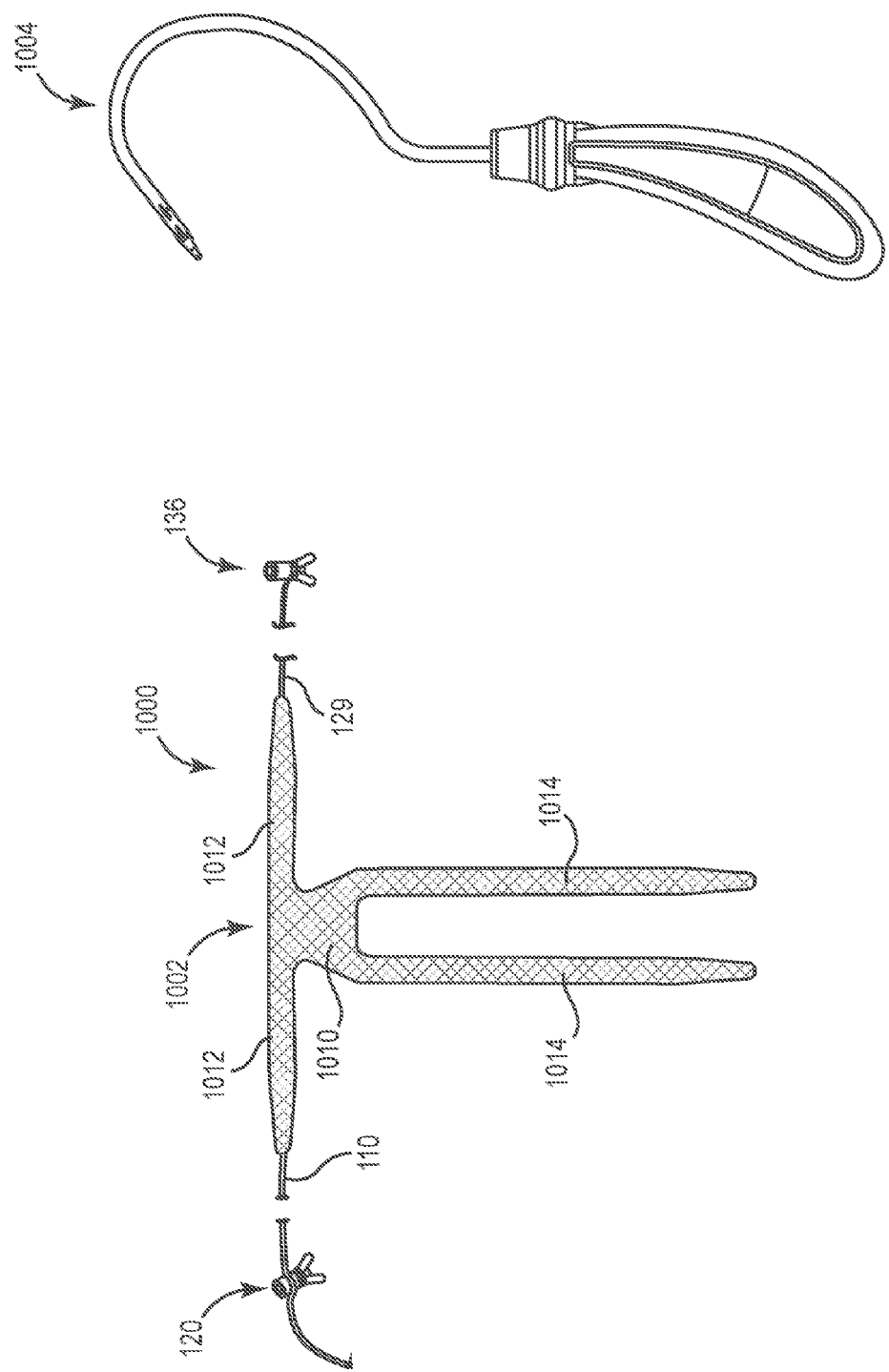
FIG. 16 is a top view of one embodiment of a system for addressing pelvic dysfunction in a male including an adjustable support member and an introducer tool.

FIG. 16 is a top view of one embodiment of a system 1000 configured to address pelvic dysfunction in a patient. Pelvic dysfunction includes male urinary incontinence, female urinary incontinence, or female pelvic organ prolapse.

In one embodiment, the system 1000 is configured to address male urinary incontinence and includes a support member 1002 and a tool 1004 configured to couple with the anchors 120, 136 to implant the support member 1002 into the patient, for example via a single incision.

In one embodiment, the support member 1002 includes a body portion 1010, and opposing trans obturator arms 1012 and suprapubic arms 1014 extending from the body portion 1010. In one embodiment, the fixed anchor 136 is attached to one of the trans obturator arms 1012 by the interconnecting member 129 and the adjustable anchor 120 is attached to the opposing one of the obturator arms 1012 by the interconnecting member 110.

As described below, the tool 1004 is employed to attach/anchor the anchors 120, 136 into membrane material of the obturator foramen such that the obturator arms 1012 extend between the opposing obturator membranes. The suprapubic arms 1014 are surgically placed suprapubically (with or without a tool).

In one embodiment, the anchor 120 is an adjustable anchor as described above and the support member 1002 includes four arms that are configured for four-point attachment to the patient to provide an adjustable support offering elevation and compression of the ventral urethral bulb of a man with compression of the perineal urethra. The support member 1002, as implanted, is configured to provide immediate beneficial relief to urinary incontinence and is also configured to allow tissue to grow into the porous structure of the support member 1002.

Figure 17:
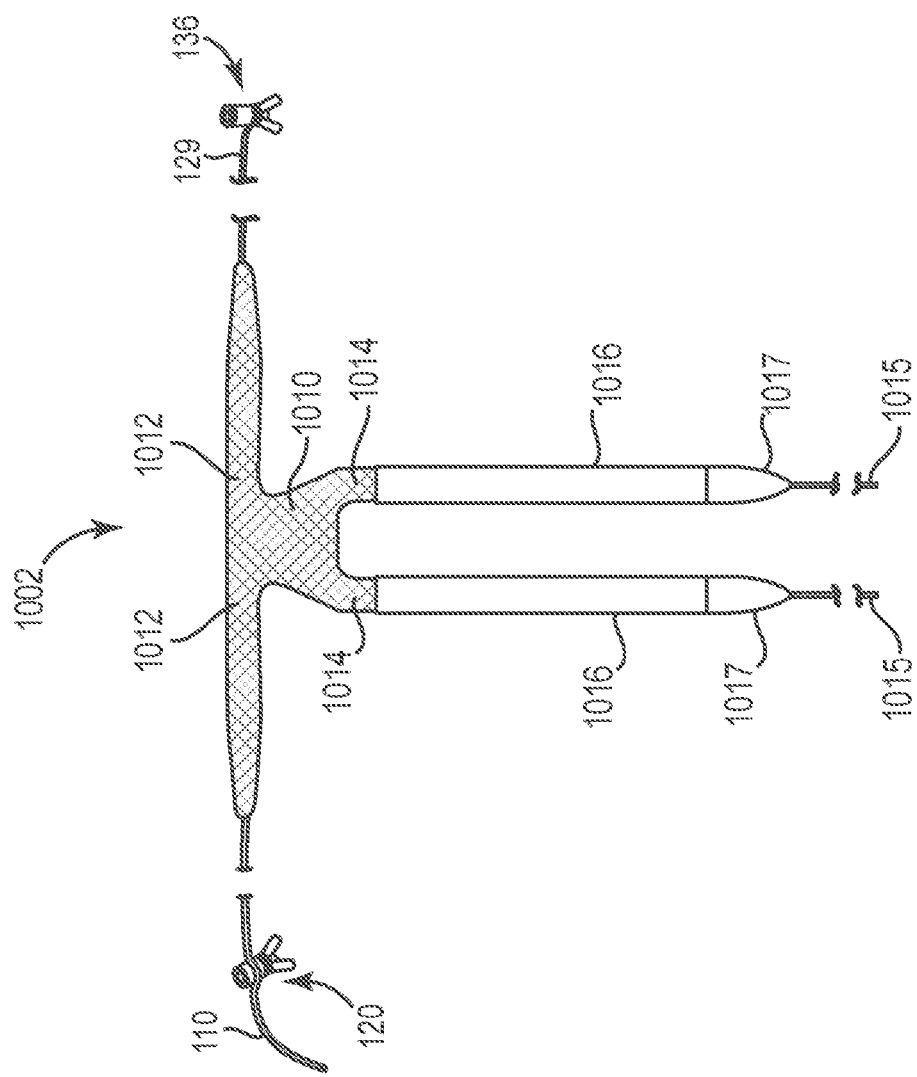
FIG. 17 is a top view of the adjustable support member illustrated in FIG. 16.

FIG. 17 is a top view of the support member 1002 modified to include optional suture lines 1015 connected to a removable tip 1017 at an end of each of the suprapubic arms 1014 and optional sleeves 1016 disposed over the arms 1014. The optional suture lines 1015 and sleeves 1016 are employed when placing the arms 1014 suprapubically within the patient with the tool 1004.

In general, the trans obturator arms 1012 are provided as a pair of opposing and aligned arms and the suprapubic arms 1014 are not parallel with the trans obturator arms 1012. Other conformations for support member 1002 are also acceptable, including more than four arms or fewer than four arms, and the relative orientation between the arms provided in the examples is not intended to limit the scope of this application.

In one embodiment, the support member 1002 is fabricated from a porous polypropylene mesh suited to allow tissue to grow into the mesh. In one embodiment, the support member 1002 includes optional sleeves 1016 disposed over the suprapubic arms 1014, for example, where the sleeves 1016 reduce friction of the arms 1014 as they are implanted within tissue of the patient. In one embodiment, the optional suture lines 1015 are braided polyester lines that are coated with a friction-reducing agent such as polytetrafluoroethylene, although other forms of suture lines and other forms of friction-reducing agents are also acceptable.

Figures 18A, 18B:
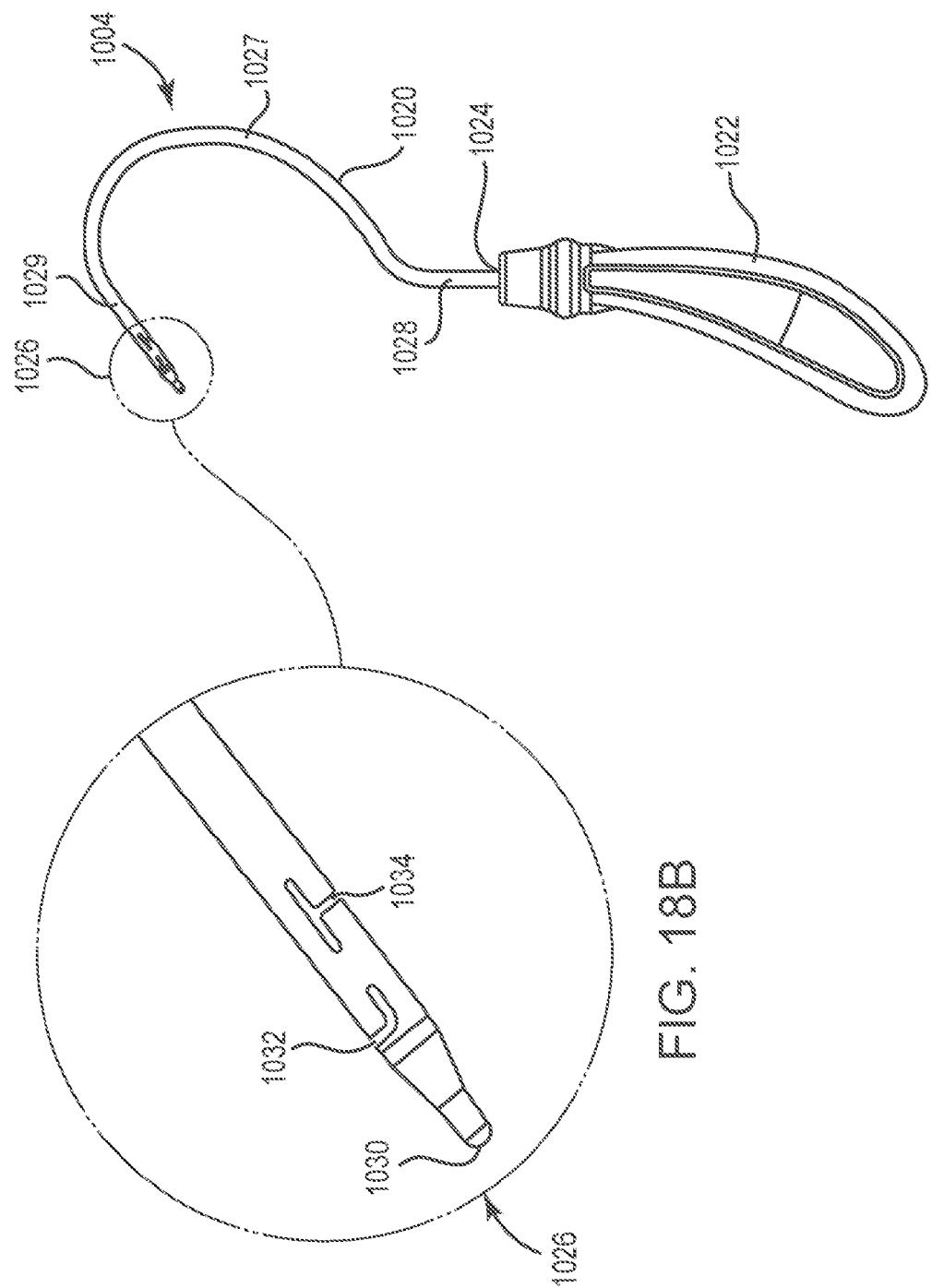
FIG. 18A is a side view of the introducer tool illustrated in FIG. 16.
FIG. 18B is a close-up view of a distal tip of the tool.

FIG. 18A is a top view of the tool 1004 and FIG. 18B is a close-up view of a distal end portion 1026 of the tool 1004.

In one embodiment, the tool 1004 includes a hook 1020 extending from a handle 1022 between a proximal end 1024 and a distal end portion 1026. The hook 1020 is a planar hook having a curve and is configured for an inside-out pass from a midline incision in the patient through a membrane tissue covering the obturator foramen. In one embodiment, the hook 1020 is formed of a suitable material, for example stainless steel, fashioned to lie in a plane (i.e., the hook 1020 is a "planar" hook) between the end 1024 and the distal end portion 1026. The illustrated embodiment of the hook 1020 in FIG. 18A is not a helical hook.

In one embodiment, the hook 1020 is a substantially solid hook (i.e., the hook does not include a lumen) having a curved section 1027 connected between a first linear section 1028 and a second linear section 1029. The curvature of the curved section 1027 is not constant as the curved section 1027 has greater curvature adjacent the second linear section 1029 as compared to the first linear section 1028. The second linear section 1029 is not parallel to the first linear section 1028, and a ray extending from and aligned with the second linear section will intersect a horizontal plane from which the proximal end 1024 of the hook 1020 extends.

The hook 1020/tool 1004 is configured to implant the support member 1002 into a male patient via an inside-out pass extending from a single perineal incision to an obturator foramen of the male patient, where the pass minimizes the possibility of undesirably perforating the urethra or the corpus cavernosa of the patient.

In one embodiment, the distal end portion 1026 of the hook 1020 (FIG. 18B) includes a distal end 1030, an L-shaped slot 1032 proximal the distal end 1030, and a T-shaped slot 1034 proximal the L-shaped slot. The hook 1020 is preferably formed from a stable material such as stainless steel and the handle 1022 is preferably formed from plastic, for example, although other materials are also acceptable.

Figure 19:
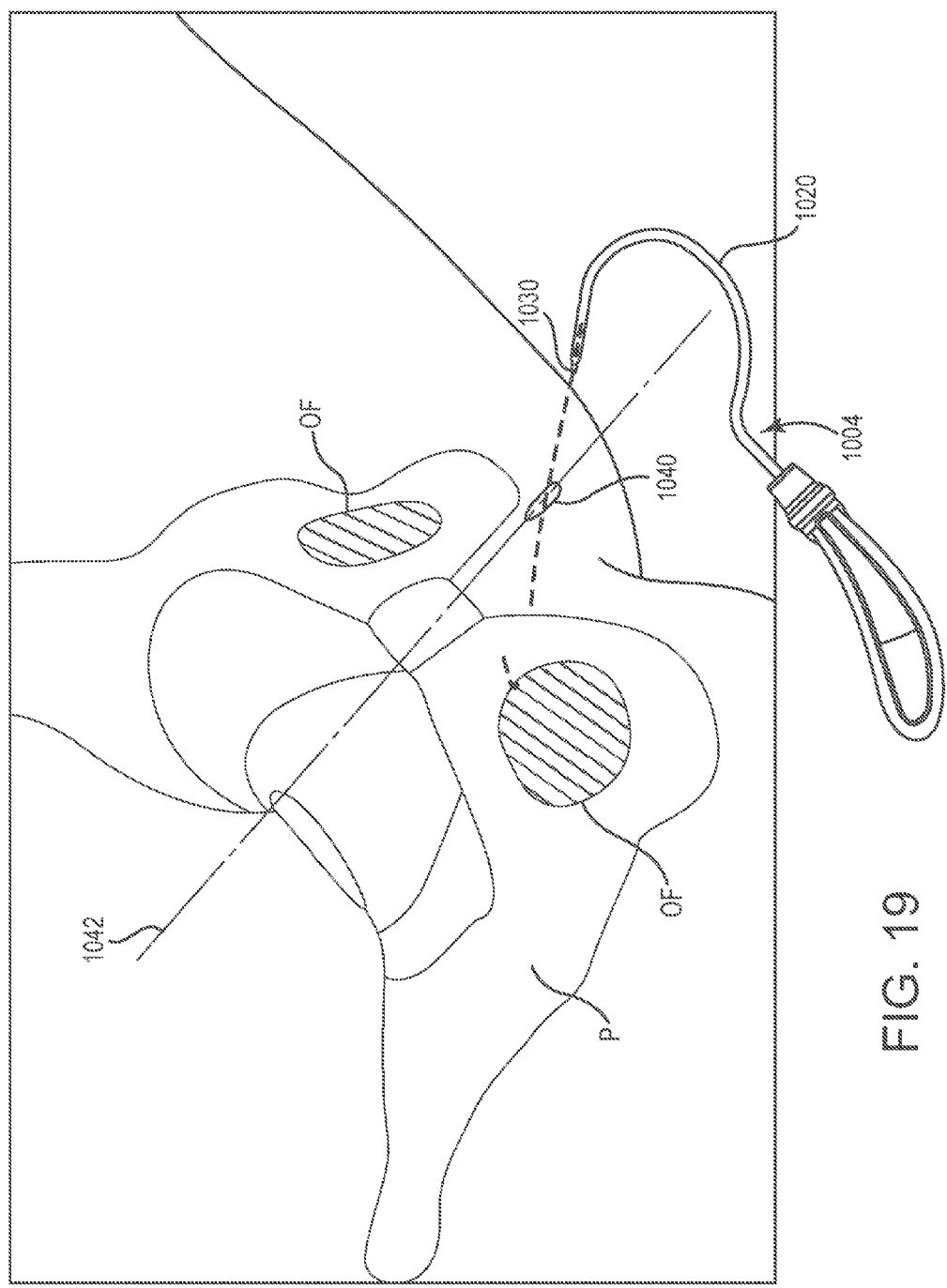
FIG. 19 is a schematic view of an inside-out insertion path for the tool entering through an incision and piercing an obturator foramen of the patient for placement of trans obturator arms of the support member.

FIG. 19 is a schematic view of a pelvis P of a patient having a pair of obturator foramen OF. The pelvis P is surgically accessed through a single, minimally invasive perineal incision 1040. A reference axis 1042 is provided that is aligned on a midline of the patient's body from the incision 1040 through the pubic symphysis. The reference axis 1042 separates the patient's body between the left side of the patient and the right side of the patient (e.g., the right side includes the illustrated obturator foramen OF).

The support member 1002 (FIG. 17) is implanted, for example, by forming the perineal incision 1040 and dissecting to isolate the bulbous urethra (for men) while ensuring that the bulbous spongiosis muscle remains intact. The surgeon will optionally, depending upon surgeon preference, dissect down to the pubic ramus to identify this landmark.

With reference to FIGS. 17 and 18B, the surgeon forms the perineal incision 1040 and employs the tool 1004 to guide each of the trans obturator arms 1012 along an inside-out path through the obturator foramen. For example, a distal end 1030 of the hook 1020 is engaged with the fixed anchor 136. The hook 1020 and the fixed anchor 136 are inserted into the perineal incision 1040, guided along an inside-out path that extends inward to a descending portion of the ramus of the patient, and into the membrane extending over the obturator foramen OF. The distal end 1030 of the hook 1020 penetrates the membrane extending over the obturator foramen OF with an audible "pop," indicating the fixed anchor 136 is attached to the membrane of the obturator foramen OF. In a similar maneuver, the distal end 1030 of the hook 1020 is engaged with the adjustable anchor 120, and the hook 1020 and adjustable anchor 120 are inserted into the perineal incision 1040, along a contra-lateral inside-out path to a descending portion of the ramus of the patient and into the membrane extending over the obturator foramen OF. Once again, when the distal end 1030 of the hook 1020 penetrates the foramen membrane an audible "pop" indicates a successful anchoring of the adjustable anchor 120 into the membrane of the obturator foramen.

In one embodiment, the suprapubic arms 1014 (having the optional sleeves 1016 of FIG. 17 removed) are inserted into the single perineal incision 1040 and tunneled into position subcutaneously within the patient. For example, the tool 1004 (or another suitable tool) is employed to insert the suprapubic arms 1014 into the incision 1040 suprapubically, at which location the arms 1014 are overlapped subcutaneously within the patient to allow tissue ingrowth to secure the support member 1002 within the patient.

Figure 20:
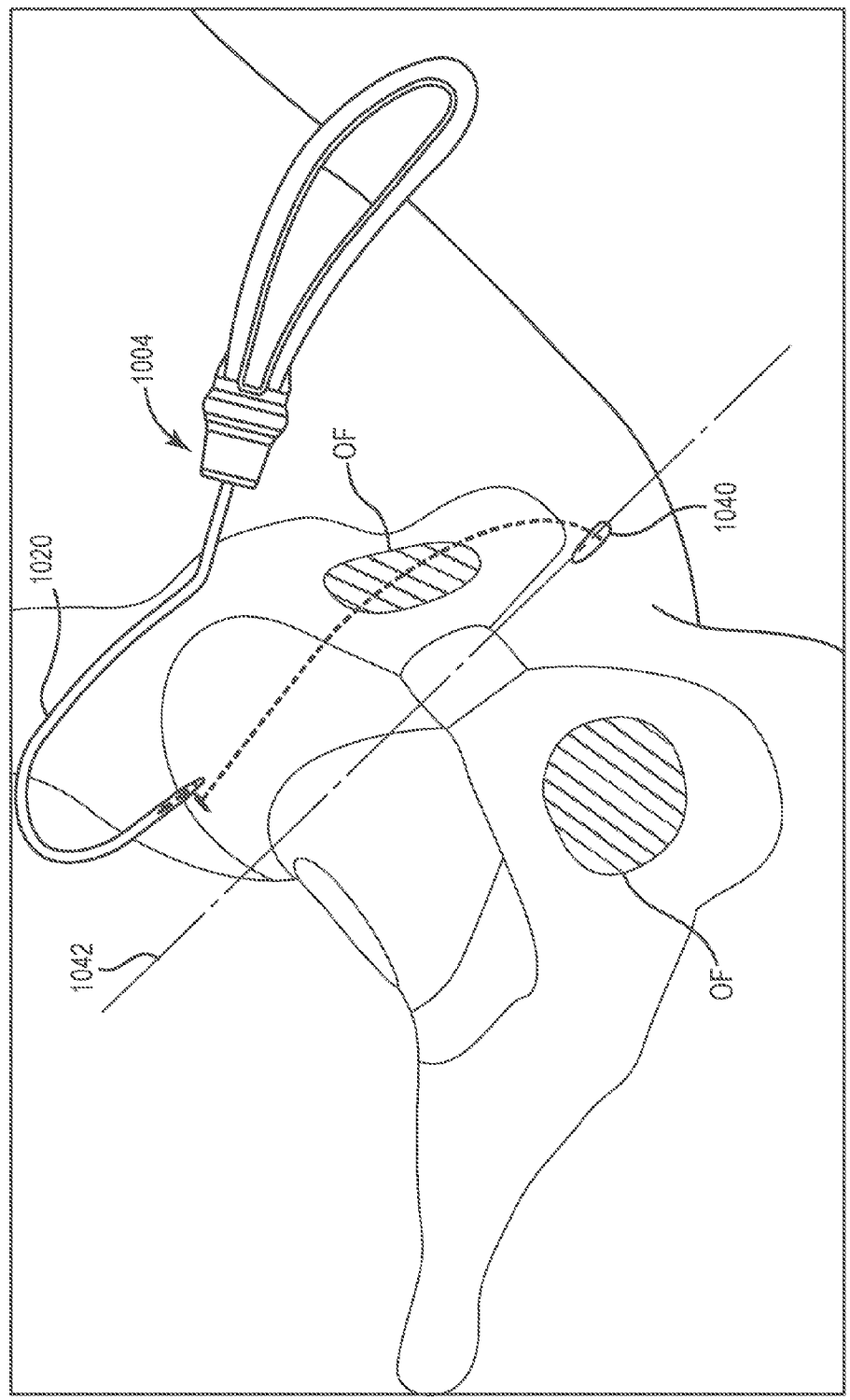
FIG. 20 is a schematic view of an insertion path for the tool taking an optional suprapubic approach from the abdomen down to the incision for placement of suprapubic arms of the support member.

With reference to FIGS. 17 and 20, in one embodiment the suprapubic arms 1014 (including the optional sleeves 1016 of FIG. 17) are implanted by the tool 1004 subcutaneously within the patient via a pre-pubic opening. For example, the distal end 1030 of the hook 1020 is inserted under the patient's skin and moved subcutaneously from the pre-pubic opening to the perineal incision 1040 lateral the urethra. One of the suprapubic arms 1014 is attached to the T-shaped slot 1034 and retracted backwards by the tool 1004 along the path from the perineal incision 1040 to the pre-pubic opening. The other suprapubic arm 1014 is implanted contra-laterally in a similar manner. Afterwards, the suture, the tip and the optional sleeves 1016 are removed from the suprapubic arms 1014 leaving the porous mesh in place for subsequent tissue ingrowth. In one embodiment, excess length of the suprapubic arms 1014 is trimmed flush with the patient's skin. In one embodiment, the suprapubic arms 1014 are crossed/overlapped one over the other subcutaneously.

The trans obturator arms 1012 are suspended/connected in a midline location between the membrane of the obturator foramen OF and the suprapubic arms 1014 are retained in a fixed position subcutaneously. In one embodiment, the interconnecting member 110 is pulled through the adjustable anchor 120 shorten the midline length between the ends of the trans obturator arms 1012 and adjust tension in the support member 1002. In this manner, support member 1002 elevates and compresses the ventral urethral bulb B of the patient. The suprapubic arms 1014 are pulled to adjust tension prior to being secured to each other, which compresses the perineal urethra U. The support member 1002 allows the surgeon to tighten or loosen the tension between the arms 1012 by adjusting the adjustable anchor 120.

Figure 21:
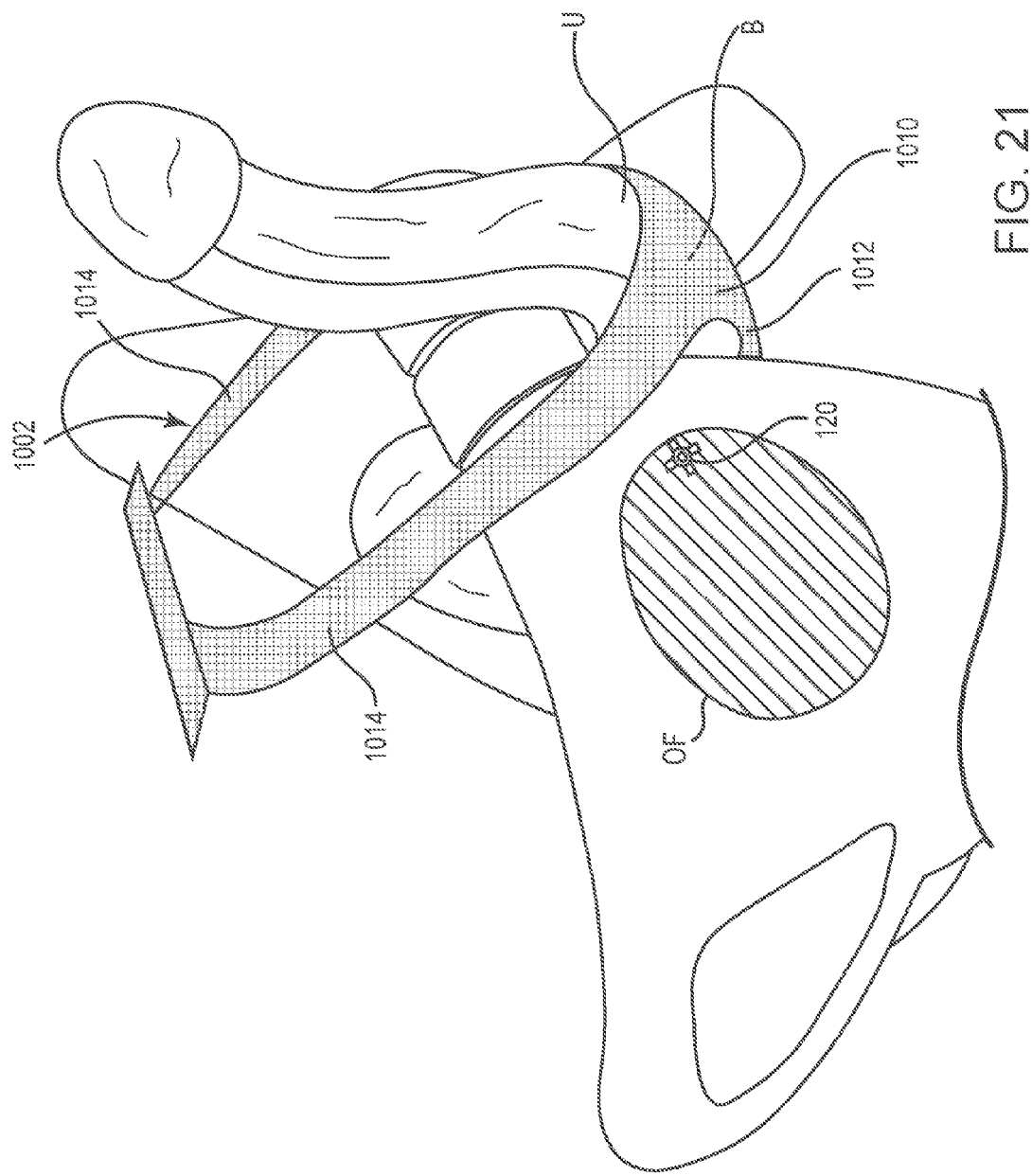
FIG. 21 is a schematic view of one embodiment of the adjustable support member illustrated in FIG. 17 as implanted via a single incision.

FIG. 21 is a schematic view of the support member 1002 implanted in a male patient. The illustration presents a sub-dermal view of the location of the support member 1002 relative to the ventral urethral bulb B of the patient. The trans obturator arms 1012 extend between membranes covering the obturator foramen OF and are adjustable via the adjustable anchor 120 to elevate and compress the ventral urethral bulb B of the patient. The suprapubic arms 1014 are tunneled subcutaneously to compress the perineal urethra U. The surgeon adjusts the tension/elevation of the support member 1002 by drawing the interconnecting member 110 through the adjustable anchor and adjusts the compression of the support member 1002 against the ventral urethral bulb B of the patient by selectively tightening the suprapubic arms 1014. This adjustment of the two pairs of arms 1012, 1014 may be done incrementally until the surgeon achieves the desired coaptation of the urethra U through the elevation and compression of the ventral urethral bulb B of the patient.

The implanted arms 1012, 1014 and the body portion 1010 allow tissue ingrowth through the support member 1002, which tends to provide a more durable and long-lasting support to address male incontinence.

The above-described approach to addressing urinary incontinence is less invasive than implanting an artificial urinary sphincter (artificial urinary sphincters can contribute to erosion of the urethra), which aids the patient to a faster recovery, and has the potential for immediate post-implantation beneficial continence results.

The adjustable anchor 120 of the support member 1002 is movable along the interconnecting member 110 to adjust the elevation of a mid-area (identified as supporting the bulbous urethra B) of the support 1002 relative to a urethra of the patient.

The elevation and compression of the urethra bulb provides Ventral Urethral Elevation (VUE) that ensures consistent placement of the support with a decreased probability of loosening. The minimal dissection of the bulbous urethra minimizes the potential for distal movement of the support member 1002. Support member 1002 is implanted through a single perineal incision 1040 that is less invasive than other surgical interventions for remedying male incontinence.

FIG. 22A is a perspective view of one embodiment of a support member 1100 including adjustable anchor 120 and a hanger 1102. In one embodiment, the support member 1100 is a substantially rectangular porous mesh termed a "tape," substantially as illustrated in FIG. 22A, and fabricated from materials similar to those described above for the sling 100 (FIG. 1). The support member 1100 is configured for implantation into a male patient or a female patient via a single midline incision (perineal for men and paraurethral or vaginal for women) and includes a mechanism for adjusting tension in the support 1100.

The adjustable anchor 120 described above is attached to the first end 102 of the support member 1100 by the interconnecting member 110, and a hanger 1102 is attached to the second end 104 of the support member. In one embodiment, the hanger 1102 is fabricated from plastic and is attached to the end 104 of the support 1100 by welding, stitching, adhesive attachment, or another suitable form of attachment.

The hanger 1102 is configured to hang over a portion of a pubic ramus of a pelvis to secure a second end 104 of the support member 1100, and the adjustable anchor 120 is attachable to a membrane extending over an obturator foramen. The interconnecting member 110 slides relative to the anchor 120 to adjust the tension and support provided by the support member 1100. The hanger 1102 is configured to be placed over a surface of the pubic bone without the use of screws. In this manner, the hanger 1102 does not penetrate the bone, which allows the surgeon to more quickly and accurately place the support 1100 inside the patient.

FIG. 22B is a side view and FIG. 22C is a front view of the hanger 1102. In one embodiment, the hanger 1102 extends between a proximal end 1110 and a distal end 1112, and includes a curved hanging portion 1114. The proximal end 1110 is attached to the end 104 of the support 1100 (FIG. 22A). In one embodiment, the distal end 1112 converges to a point that is configured to penetrate the obturator foramen membrane and allow the hanging portion 1114 to engage with and drape over a pubic ramus. The hanging portion 1114 is curved to correspond to a curvature of the pubic ramus bone of the pelvis.

Figure 23:
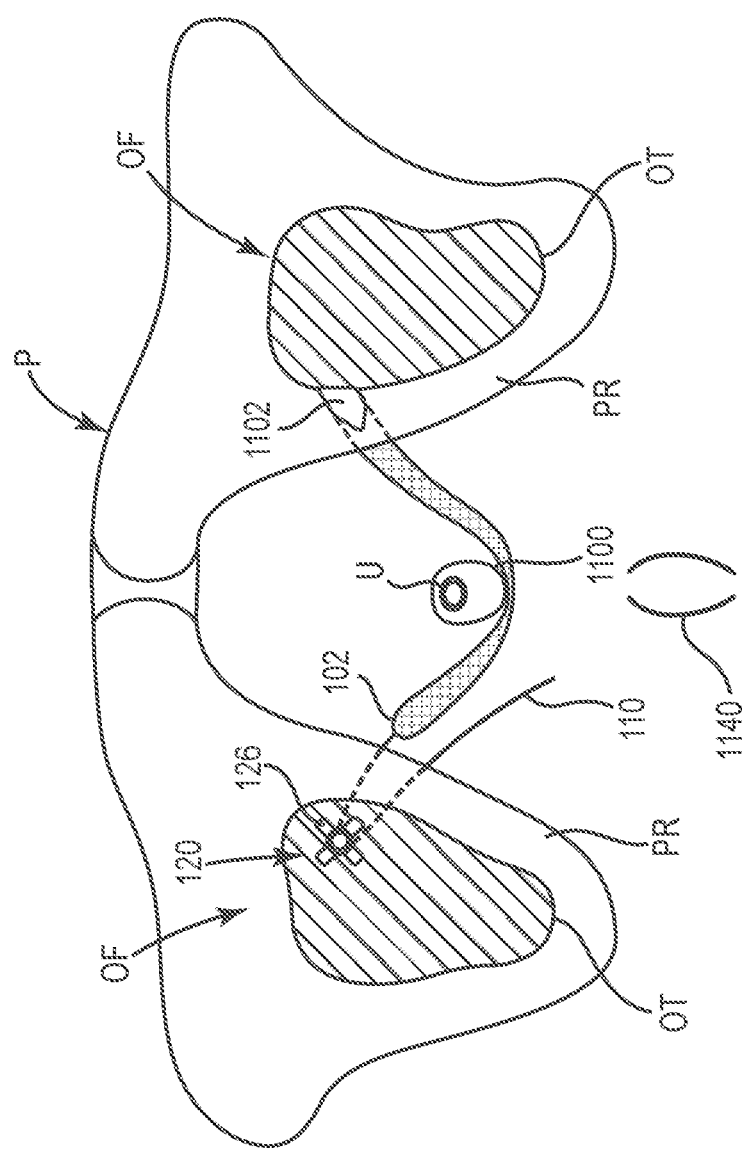
FIG. 23 is a schematic view of one embodiment of the support member illustrated in FIG. 22 implanted via a single incision with the adjustable anchor inserted in a membrane of an obturator foramen and the hanger secured over a portion of a ramus to allow the support member to alleviate pelvic dysfunction.

FIG. 23 is a schematic view of the support member 1100 attached between a pubic ramus PR of the pelvis P and tissue OT of the obturator foramen OF to support a urethra U of the patient. In one embodiment, the patient is a female and the support member 1100 supports the urethra U without compressing the urethra U. In one embodiment, the patient is a male and the support member 1100 supports the urethra U by elevating and compressing at least a portion of a bulb the urethra U.

It is to be understood that it is undesirable to dissect tissue away from and expose the urethra U (which can contribute to urethral erosion). The illustration of the figures shows a urethra U with a thickness to indicate tissue is still surrounding the urethra.

In one embodiment, the hanger 1102 is introduced through a single perineal incision 1140 along an inside out pass that places the hanger 1102 around a portion of the pubic ramus PR. For example, the surgeon places the hanger 1102 either digitally with a finger, or with a tool, into the incision 1140 and guides the hanger 1102 inward against the membrane covering the obturator foramen, after which the surgeon penetrates the membrane with the pointed distal end 1112 (FIG. 22C) of the hanger 1102. Movement of the pointed distal end 1112 of the hanger 1102 through the obturator foramen membrane positions the hanging portion 1114 for engagement over the pubic ramus PR.

The adjustable anchor 120 is guided through the incision 1140 with the tool 1004 (FIG. 18A) as described above in FIG. 19. The tension of the support member 1100 is adjusted by pulling on the interconnecting member 110 until a desired length of the support member 1100 is achieved that provides support to the tissue around the urethra U, as described above. In this manner, the adjustable anchor 120 of the support 1100 allows the elevation of mid-area of the support 1100 under the urethra to be adjusted to support the urethra without displacing or compressing the urethra (as desirable in a female). The surgeon closes the minimally invasive single incision 1140 according to acceptable practices. The support provides the patient with a state of continence immediately after implantation due to the support or support and elevation of the urethra U.

Figure 24:
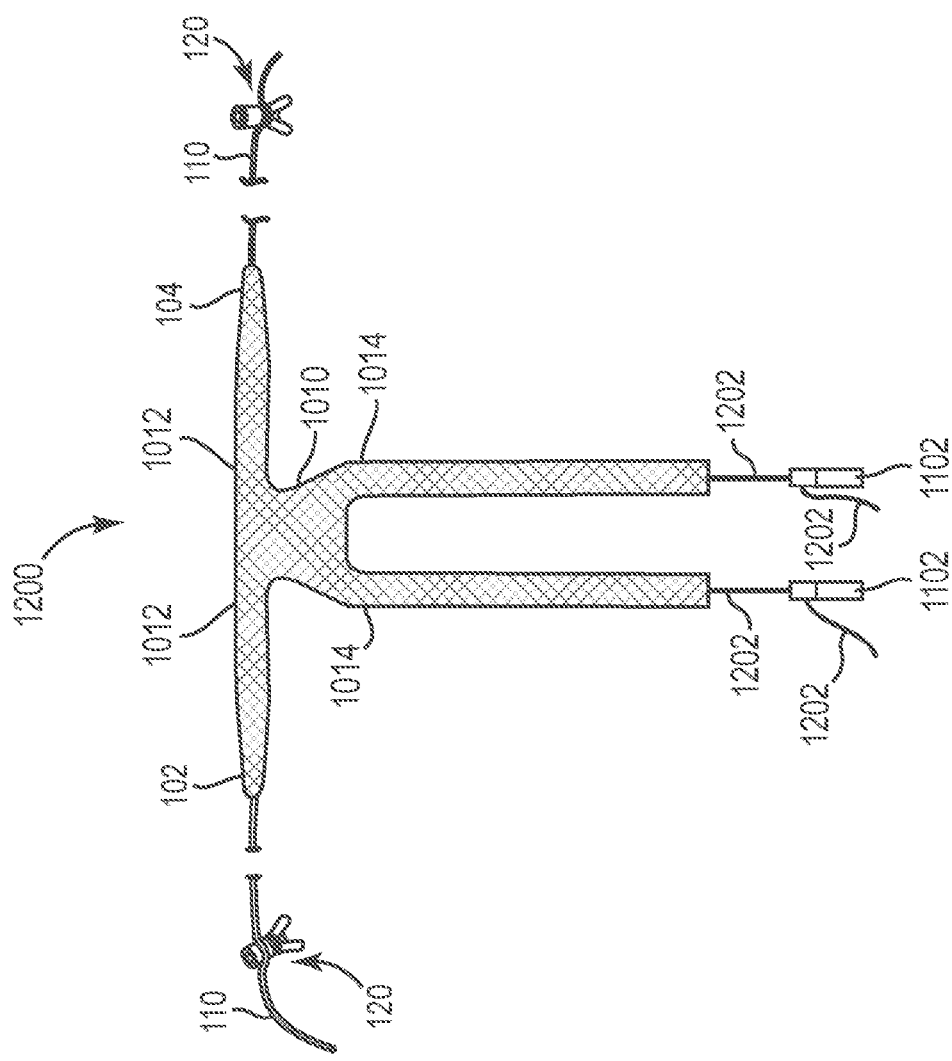
FIG. 24 is a top view of one embodiment of a support member including adjustable anchors and hangers and implantable via a single incision.

FIG. 24 is a top view of one embodiment of a support member 1200 including adjustable anchors 120 and adjustable hangers 1102 that allow the support 1200 to be implantable via a single incision. The support member 1200 is similar to the support member 1002 (FIG. 17) and includes the body portion 1010, and opposing trans obturator arms 1012 and suprapubic arms 1014 extending from the body portion 1010.

In one embodiment, an adjustable anchor 120 is attached to each of the opposing trans obturator arms 1012 by an interconnecting member 110, and the adjustable hanger 1102 is attached to each of the suprapubic arms 1014 by an adjustable suture 1202. The adjustable suture 1202 is configured to allow the independent adjustment of the distance between each hanger 1102 and the arm 1014 to which it is attached in a manner similar to that described above in FIGS. 2-4, for example. For example, the adjustable hanger 1102 is movable distally and proximally along the suture line 1202 to allow for the selected and independent adjustment of the hanger 1102 relative to the support 1200. The support member 1200 is configured for implantation into the patient via a single incision, and as such, the optional sleeves 1016 (FIG. 17) covering one or more of the arms are not provided on the support member 1200.

The support member 1200 is fabricated from the materials described above, and in one embodiment is provided as a porous polypropylene mesh having a pore size of about 665 micrometers, a porous area of about 42.3% of the total area, a basis weight of about 119 g/m$^2$, and a thinness of about 635 micrometers.

The adjustable anchors 120 and hangers 1102 are as described above. It is to be understood that the support 1200 could be provided with four adjustable anchors 120 or four adjustable hangers 1102, or combinations of adjustable anchors and hangers. During implantation, the surgeon selectively and independently adjusts each anchor 120 and each hanger 1102 by sliding the adjustable component along its respective line 110, 1202 to achieve the desired amount of support or elevation or compression of the implanted support 1200 relative to the patient's anatomy.

Figure 25:
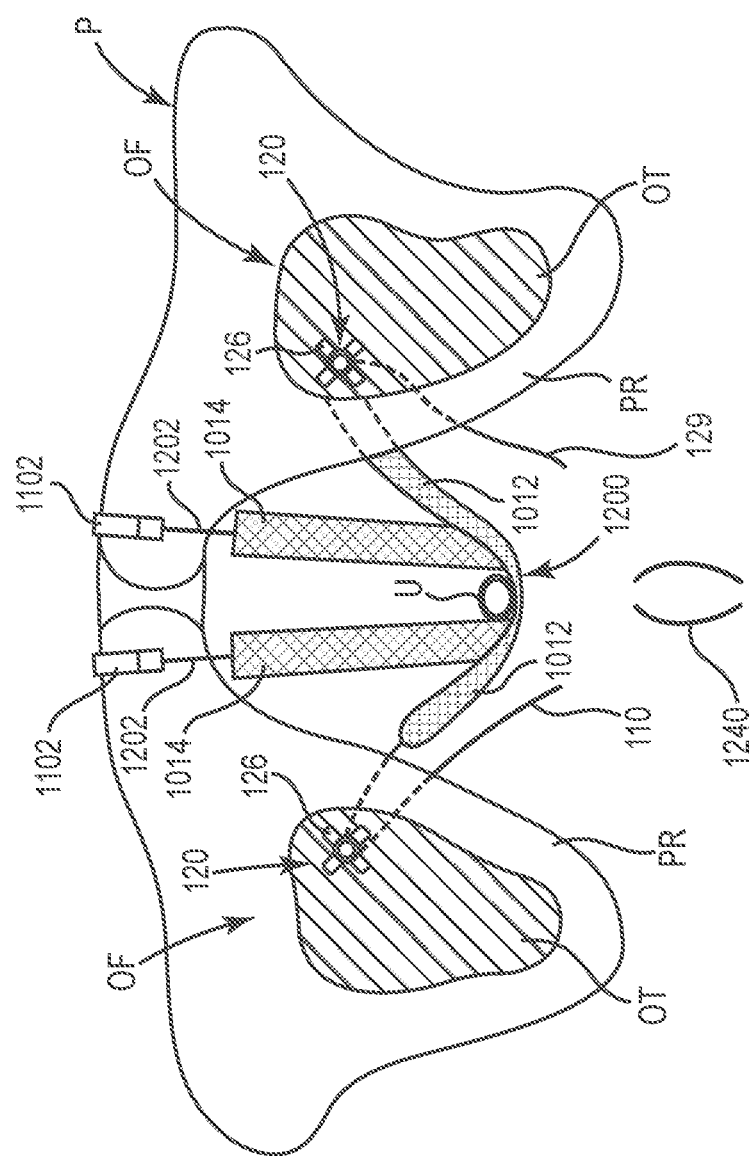
FIG. 25 is a schematic view of one embodiment of the adjustable anchors of FIG. 24 anchored to membranes of obturator foramen and the hangers secured to the pelvis.

FIG. 25 is a schematic view of one embodiment of the support member 1200 having the adjustable anchors 120 attached to membranes of obturator foramen OF and the hangers thousand 102 secured to the pelvis P.

In one embodiment, support member 1200 is implanted into the pelvis of the patient through a single midline incision 1240. In a male example, the adjustable anchors 120 are implanted through a perineal incision of a man and attached to the membrane tissue OT extending over the obturator foramen OF by the tool 1004 (FIG. 16) via the approach described above. In a female example, the adjustable anchors 120 are implanted through a vaginal incision of a woman and attached to the membrane tissue OT extending over the obturator foramen OF by the tool 1004 (FIG. 16) via the approach described above.

In particular, one of the adjustable anchors 120 is attached to the distal end 1030 of the tool 1004, the distal end 1030 and the adjustable anchor 120 are inserted through the incision 1240 and guided to a location superior the pubic ramus PR where the tool 1004 forces the adjustable anchor 120 into the membrane OT of the obturator foramen OF to attach one of the trans obturator arms 1012 to the patient. A similar maneuver is carried out on the contra-lateral side of the patient to implant the other of the trans obturator arms 1012.

In one embodiment, suprapubic arms 1014 are each inserted individually and guided suprapubically and subcutaneously to a prominence of the pelvis P over which the anchors 1102 are hung. The suture line 1202 is adjusted to place the arm 1014 in the desired location. Alternatively, a tool or other device is employed to guide the hangers 1102 subcutaneously to the pelvis P.

The anchors 120 are adjusted to support to the urethra U by sliding one (or both) of the interconnecting members 110 through a respective one of the adjustable anchor 120 after implantation of the support member 1200 in the manner described above. In this manner, tension provided by the support member 1200 relative to the urethra U is adjustable by the surgeon to achieve compression and elevation of the urethra U in a man or support without compression of the urethra in a woman. Each of the adjustable anchors 120 is individually adjustable to allow the urethra U to be centered relative to the trans obturator arms 1012.

Figure 26:
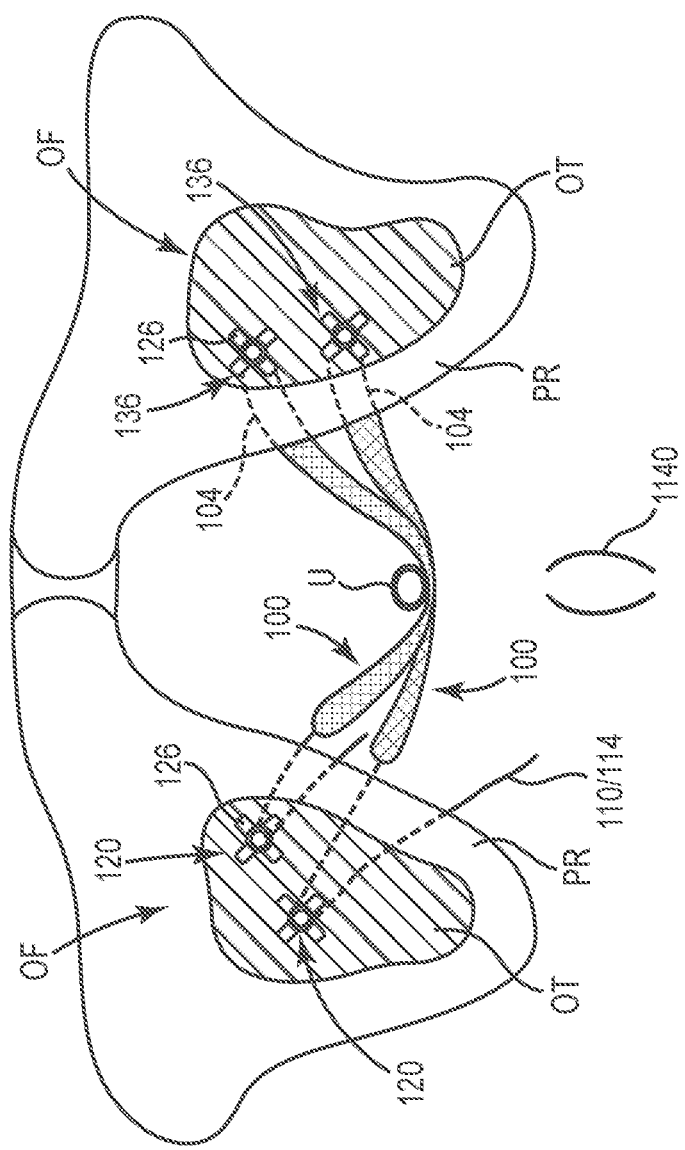
FIG. 26 is a schematic view of a pair of adjustable supports as illustrated in FIG. 1 implanted into a patient via a single incision to alleviate pelvic dysfunction.

FIG. 26 is a schematic view of a pair of adjustable slings 100 as illustrated in FIG. 1 implanted into a patient via a single incision 1140 to alleviate pelvic dysfunction.

In one embodiment, two or more slings 100 are implanted into a male patient through a single minimally invasive perineal incision 1140 (for example with tool 1004) and held in place by anchors 120, 136. The adjustable anchor 120 permits each sling 100 to be adjusted. In addition, each sling 100 is configured to be selectively positioned by the surgeon to provide elevation and compression of the urethral bulb around the urethra U of a male patient.

In one embodiment, two or more slings 100 are implanted into a female patient through a single minimally invasive vaginal incision 1140 (again, with the tool 1004) and held in place by the anchors 120, 136. The adjustable anchor 120 permits each sling 100 to be adjusted. The surgeon may selectively position each sling 100 to provide support for the urethra of the female without compression of the urethra, which can undesirably erode the short female urethra.

By the embodiments described above, adjustable slings and supports are provided that are configured to be implanted into the patient (male or female) through one minimally invasive single incision. The adjustable support provides an immediate remedy to the incontinence of the patient because of the tensioned and adjustable arms in combination with the rapid healing of the minimally invasive procedure.

It is to be again appreciated that components of these devices could be reversed, if desired, in a right side/left side sense from their arrangements as shown in the examples of FIGS. 1 and 5. It is also to be appreciated that method steps could be performed in other sequences.

It is also to be appreciated that the examples of methods described herein, for surgical placement of devices for anatomical support, do not require skin exits or incisions other than for a single vaginal incision (or, in a male patient, a single perineal incision) for placement and adjustment.

Upon occurrence of tissue in-growth, after implantation surgery is completed and during the patient's healing process, anchors might then become unnecessary to continue to secure the anatomical support device in the patient. Therefore, any of the anchors and the interconnecting members could be made of a suitable medical grade bioresorbable material.

It is to be also appreciated that the foregoing examples of implantable devices for anatomical support provide means for adjustment or tensioning of anatomical support members that are not dependent upon anchor placement. For example, increased tensioning of the devices may be advantageously achieved without a need for advancing anchors more deeply into target tissue in the patient. Also, the aforedescribed frictional sliding engagement between interconnecting member 110 and adjustable anchor 120—or between interconnecting member 110 and tensioning element 530—permits novel intraoperative adjustment of the implantable devices for anatomical support disclosed herein. Furthermore adjustable anchor 120, as well as the combination of anchor 520 with tensioning element 530, permits such intraoperative adjustment to be performed as many times as desired during a particular implantation procedure, to achieve optimal device placement, adjustment, and tensioning.

Devices for treatment of pelvic organ prolapse are surgically implanted to inhibit prolapse of the supported organ. However, some devices provide unreliable anatomical fixation or unacceptable adjustment or tensioning, any one condition of which could result in suboptimal or even unacceptable results in the treatment of organ prolapse.

The following exemplary embodiments provide a sacrocolpopexy support to treat prolapse of the vagina, particularly after hysterectomy surgery, and a method of treating prolapse of the vagina.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

One aspect provides a method of treating prolapse of a vagina that includes securing a base of a support to tissue by inserting an anchor into the tissue, the anchor coupled to the support via an interconnecting member. The method additionally includes securing a leg of the support that extends from the base of the support to a cuff of the vagina, and adjusting elevation of the cuff of the vagina relative to a patient's sacrum by sliding the interconnecting member relative to the anchor.

One aspect provides a sacrocolpopexy support including a body having a base and a leg extending from the base that is attachable to a cuff of a vagina, a first interconnecting member coupled to the base of the sacrocolpopexy support, and an adjustable anchor attachable to a ligament. The adjustable anchor is slidably coupled to the first interconnecting member to permit bi-directional movement along the first interconnecting member, and is configured to exert a compressive force generating frictional interference with the first interconnecting member so as to inhibit the bi-directional movement of the adjustable anchor along the first interconnecting member until sufficient force is applied to overcome the frictional interference.

Figure 27:
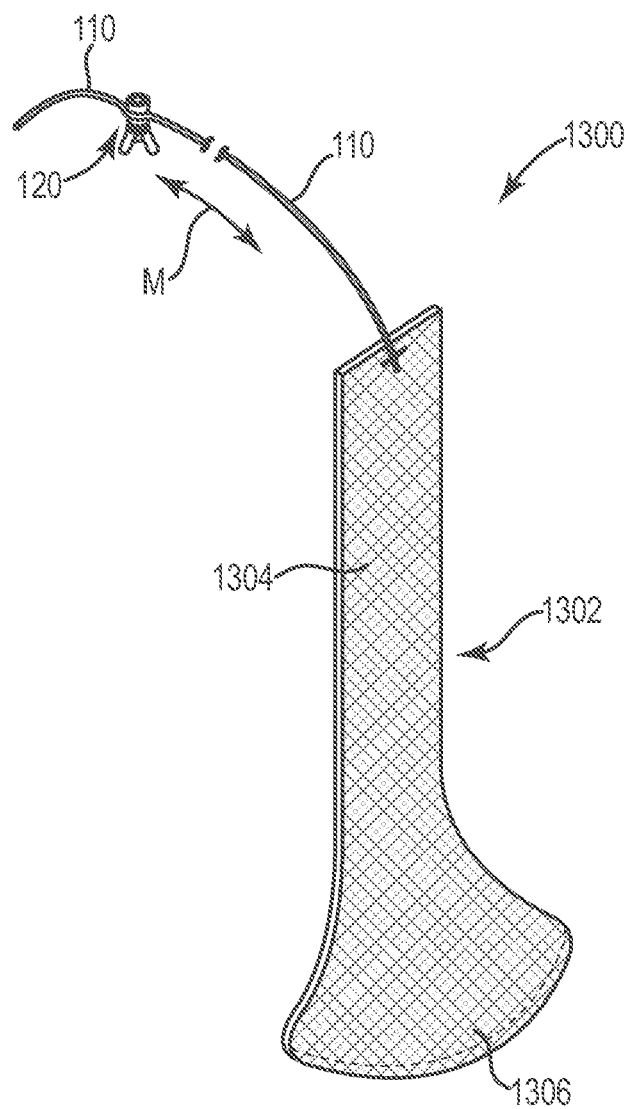
FIG. 27 is a perspective view of one embodiment of a sacrocolpopexy support.

FIG. 27 is a perspective view of one embodiment of a sacrocolpopexy support 1300. The sacrocolpopexy support 1300 (support 1300) includes a body 1302 having a base 1304 and a leg 1306 extending from the base 1304, with the interconnecting member 110 and the adjustable anchor 120 described above coupled to the base 1304. The interconnecting member 110 is attached to the base 1304 and the adjustable anchor 120 is movable along the interconnecting member 110 in a bidirectional manner as indicated by M. The adjustable anchor 120 is configured as described above to exert a compressive force that generates fictional interference with the interconnecting member 110 to inhibit the bidirectional movement of the anchor 120 until a sufficient, triggering force is applied to overcome the frictional interference. In this manner, after the surgeon attaches the leg 1306 to a cuff of the vagina and anchors the adjustable anchor 120 into a ligament or other tissue, the support 1300 is fixedly adjustable to provide the desired amount of upward support to treat vaginal vault prolapse.

The adjustment of the support 1300 is achieved by sliding the interconnecting member 110 through the adjustable anchor 120 as the surgeon tugs on the interconnecting member 110, thus positioning and tensioning the body 1302 in the desired location. Thereafter, the frictional interference of the adjustable anchor maintains the support 1300 at its desired location.

The support 1300 is typically implanted via a laparoscopic procedure in which the leg 1306 is sutured to the cuff of vagina and the adjustable anchor 120 is inserted into a ligament or other tissue, for example via tool 1004 described above. The adjustability of the interconnecting member 110 and the body 1302 advantageously allows positioning the support 1300 symmetrically relative to the bilateral line of symmetry defined by the patient's sacrum, or alternatively, allows positioning of the support 1300 asymmetrically relative to the bilateral line of symmetry defined by the patient's sacrum.

Typical sacrocolpopexy supports have one end that is attached to the sacrum, for example via a bone screw. Sacrocolpopexy supports anchored to the scrum offer little or no adjustability. In contrast, the support 1300 described herein is adjustable whether positioned symmetrically or asymmetrically, which offers the surgeon improved implantation approaches and has the potential to offer the patient improved outcomes.

Figure 28:
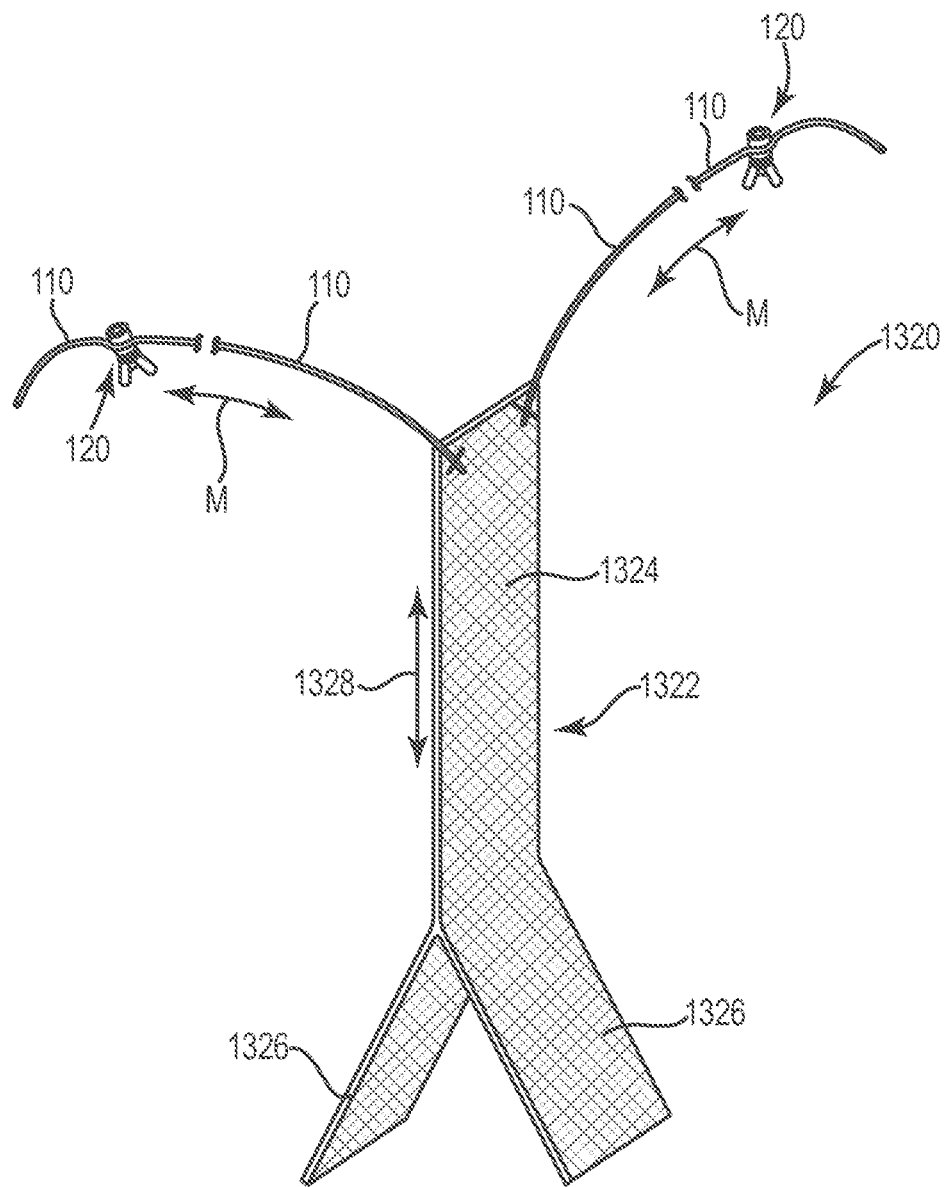
FIG. 28 is a perspective view of one embodiment of a Y-shaped sacrocolpopexy support.

FIG. 28 is a perspective view of one embodiment of a sacrocolpopexy support 1320. The sacrocolpopexy support 1320 (support 1320) is provided as a Y-shaped support that includes a body 1322 having a base 1324 and a pair of legs 1326 that extend from the base 1324, and the interconnecting member 110 and the adjustable anchor 120 described above. The interconnecting member 110 is attached to the base 1324 and the adjustable anchor 120 is movable along the interconnecting member 110 in a bi-directional manner as indicated by M.

In one embodiment, multiple interconnecting members 110 each having an adjustable anchor 120 are attached to the base 1324. FIG. 28 illustrates a pair of adjustable interconnecting members 110/adjustable anchors 120, although a single connector/anchor or more than two connector/anchor pairs are also acceptable.

In one embodiment, the body 1322 is provided as a non-planar Y-shaped body and the base 1324 is an elongated base disposed in a plane 1328, wherein each leg 1326 is bifurcated away from the plane 1328 at a nonzero acute angle. That is, the body 1322 provides a specific three-dimensional shape. Each of the legs 1326 is provided and positioned for attachment to an exterior surface of the cuff of vagina.

The body 1322 is selected to be bio-compatible with implantation into a human body. Suitable materials for the body 1322 include synthetic materials such as woven fabrics/meshes, nonwoven fabrics/meshes, fibrillated fibers, or spun and fibrillated fibers that are provided with voids (pores) configured to allow tissue ingrowth into the body 1322. If provided, the pores are generally larger, on average, than 75 µm to facilitate tissue in-growth through the body 1322.

In one embodiment, the body 1322 is a monofilament polypropylene mesh provided as an approximately 225 cm$^2$ mesh having a weight of approximately 21 g/m$^2$ with a pore size of approximately 1121 µm and a thickness of approximately 260 µm. This mesh is thin and light weight (i.e., the basis weight is less than approximately 30 g/m$^2$) to provide a thin and comfortable mesh that is less likely to erode tissue that contacts the mesh and less likely to be sensed by the patient through tissue layers. Other suitable materials for body 1322 include fabrics formed from polyester, polyethylene, silicone, urethanes, polyurethanes, copolymers, or block copolymers of these or suitably similar polymeric materials. Suitable such knitted monofilament polypropylene mesh is available from Coloplast Corp., Minneapolis, Minn. Other suitable woven polypropylene mesh material is available from, for example, HerniaMesh, Chivasso, Italy.

In one embodiment, the body 1322 is formed as a monolithic structure to include the base 1324 and the legs 1326. The monolithic structure of the body 1322 has no seams or weld lines, but is instead fabricated as a single, uninterrupted, continuous unit.

Figure 29A:
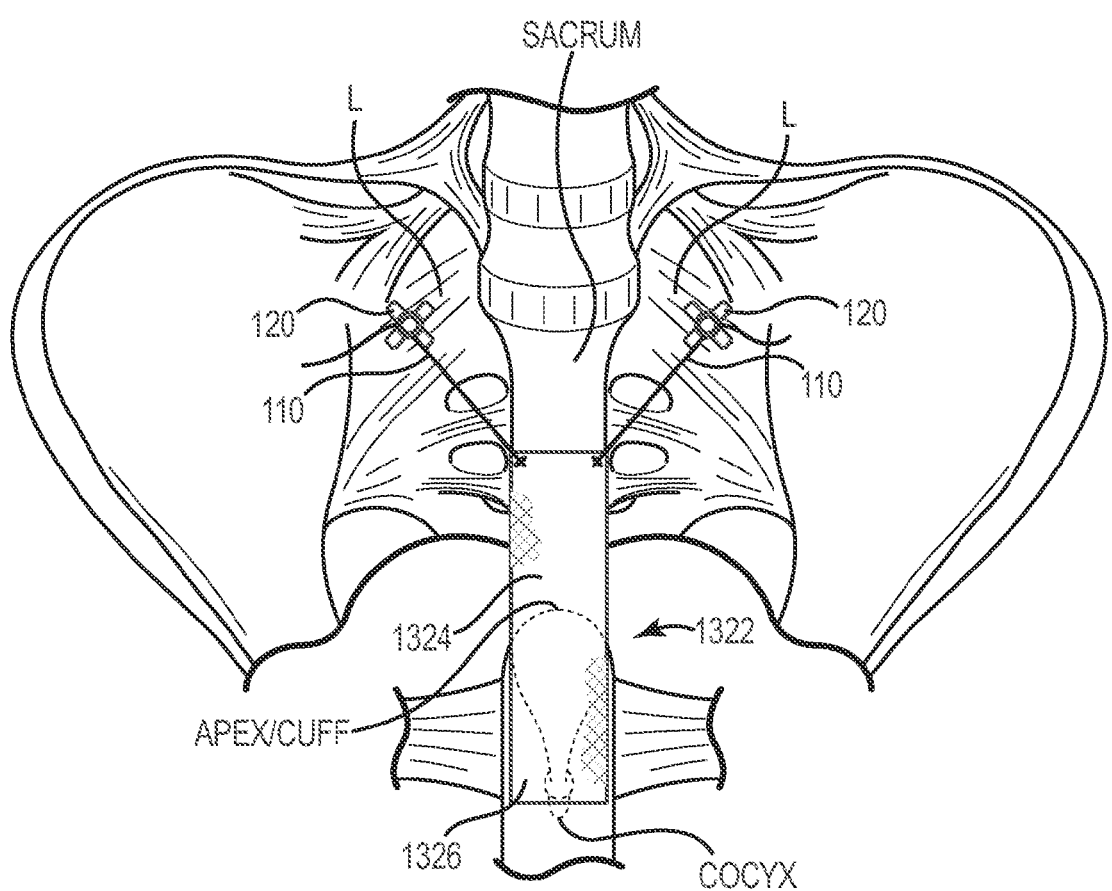
FIG. 29A is a schematic front view and FIG. 29B is a schematic side view of the Y-shaped sacrocolpopexy support illustrated in FIG. 28 symmetrically attached to ligaments to support a cuff of vagina according to one embodiment.
Figure 29B:
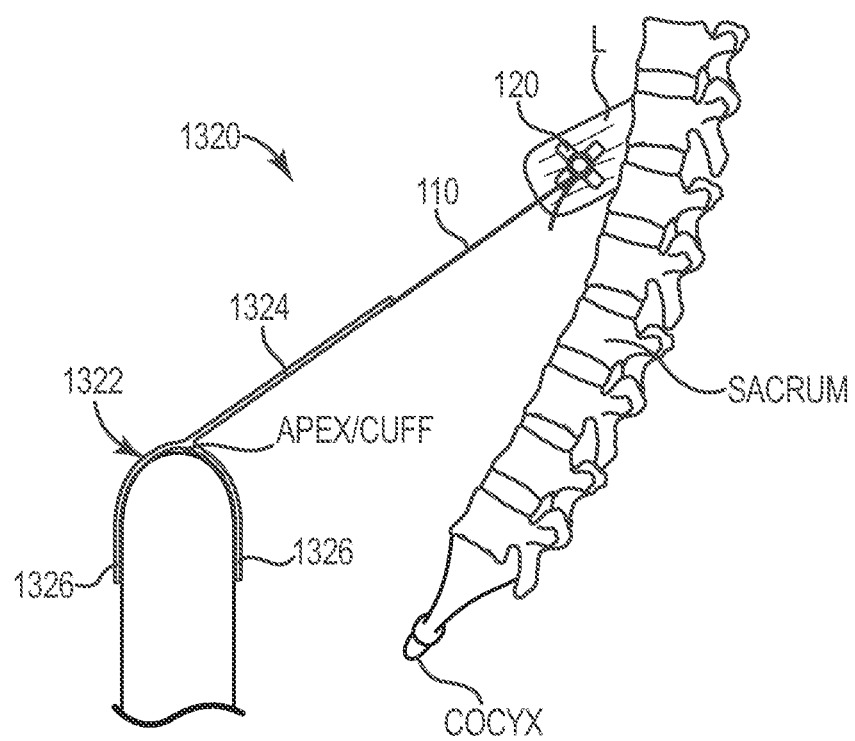

FIG. 29A is a schematic front view and FIG. 29B is a schematic side view of the Y-shaped sacrocolpopexy support 1320 symmetrically attached to ligaments L to support the vagina according to one embodiment. The support 1320 is particularly well-suited to treat vaginal vault prolapse that can arise after a hysterectomy.

One example of a method of treating prolapse of the vagina includes attaching the legs 1326 to the cuff or apex of the vagina and then securing the base 1324 to tissue, such as a ligament L, by inserting the anchor 120 through the tissue and leaving the interconnecting member 110 slackened. The cuff of the vagina is elevated to a desired location by the surgeon and the slack in the interconnecting member 110 is taken up by sliding the member 110 through the anchor 120, which results in the cuff of the vagina being supported by the ligaments L and the support 1320.

In one embodiment, a first one of the anchors 120 is inserted into a first one of the anterior sacroiliac ligaments L and a second one of the anchors 120 is inserted into an adjacent one of the anterior sacroiliac ligaments L (e.g., an anterior longitudinal ligament) to provide symmetric support to the cuff of vagina via the body 1322. This approach results in the support 1320 being implanted symmetrically relative to a line of bi-lateral symmetry defined by the patient's sacrum. The surgeon is permitted to independently adjust each one of the interconnecting members 110 relative to its respective anchor 120 to achieve the desired elevation and support of the cuff of the vagina.

FIG. 29B illustrates the support 1320 in tension between the apex/cuff of the vagina and the ligament L. It is to be understood that some amount of sag or curvature is acceptable and can exist in the base 1324 and member 110 of the support 1320 as it is stretched from the apex/cuff to the ligament L.

Figure 30:
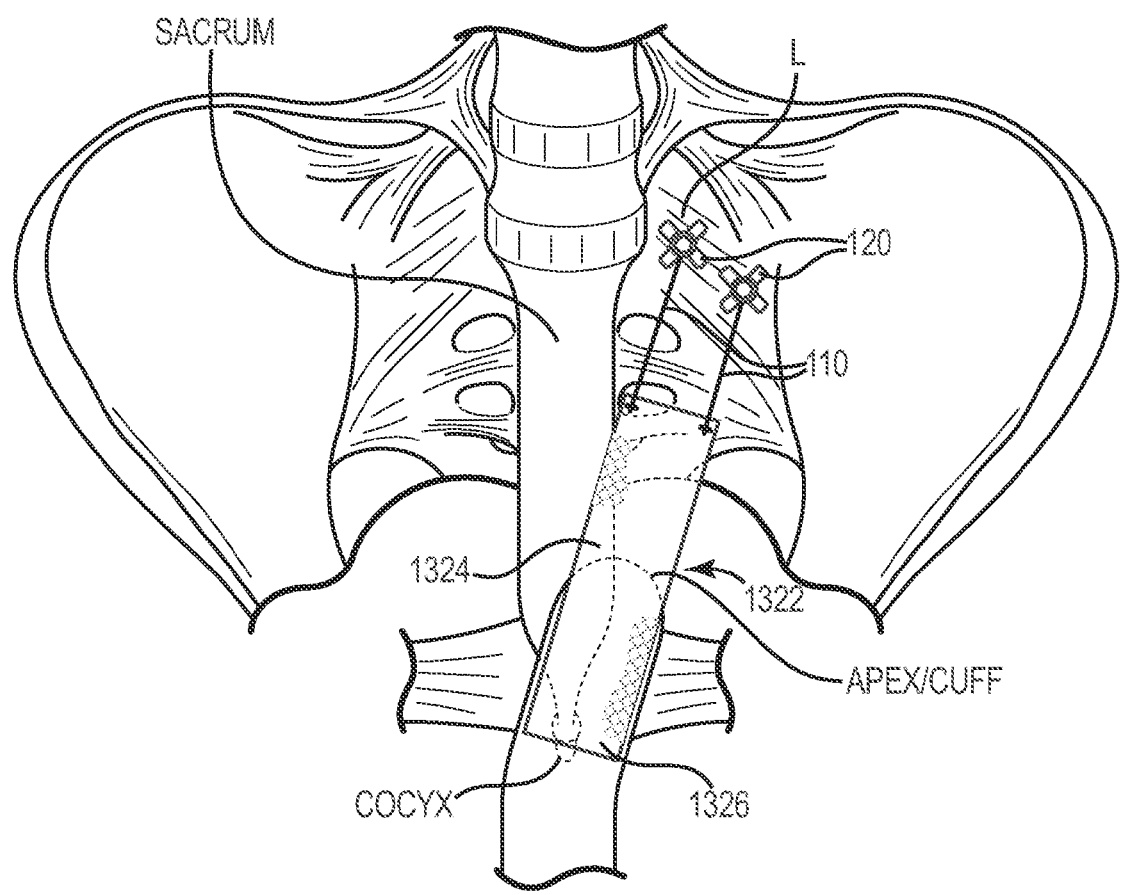
FIG. 30 is a schematic diagram of the Y-shaped sacrocolpopexy support illustrated in FIG. 28 asymmetrically attached to ligaments to support a cuff of vagina according to one embodiment.

FIG. 30 is a schematic diagram of the Y-shaped sacrocolpopexy support 1320 asymmetrically attached to one of the anterior sacroiliac ligaments L to support the cuff of vagina according to one embodiment. The legs 1326 are attached to the cuff of the vagina as described above, and both of the anchors 120 have been inserted into the ligament L. The anchors 120 need not be attached one to each side of the scrum, but instead are suited for attachment to tissue as the surgeon sees fit. In one approach, it is recommended that the surgeon elevate the cuff of vagina by sliding each interconnecting member 110 through its respective anchor, thus lifting and supporting the cuff of vagina. The cuff or the apex of vagina is supported asymmetrically relative to a line of bi-lateral symmetry that is anatomically defined by the sacrum. The remaining portions of vagina are located in the typical anatomical position. The asymmetric support of the cuff of vagina is beneficial to some patients suffering from prolapse of vaginal vault and offers the surgeon additional therapeutic approaches in treating procidentia.

Figure 31:
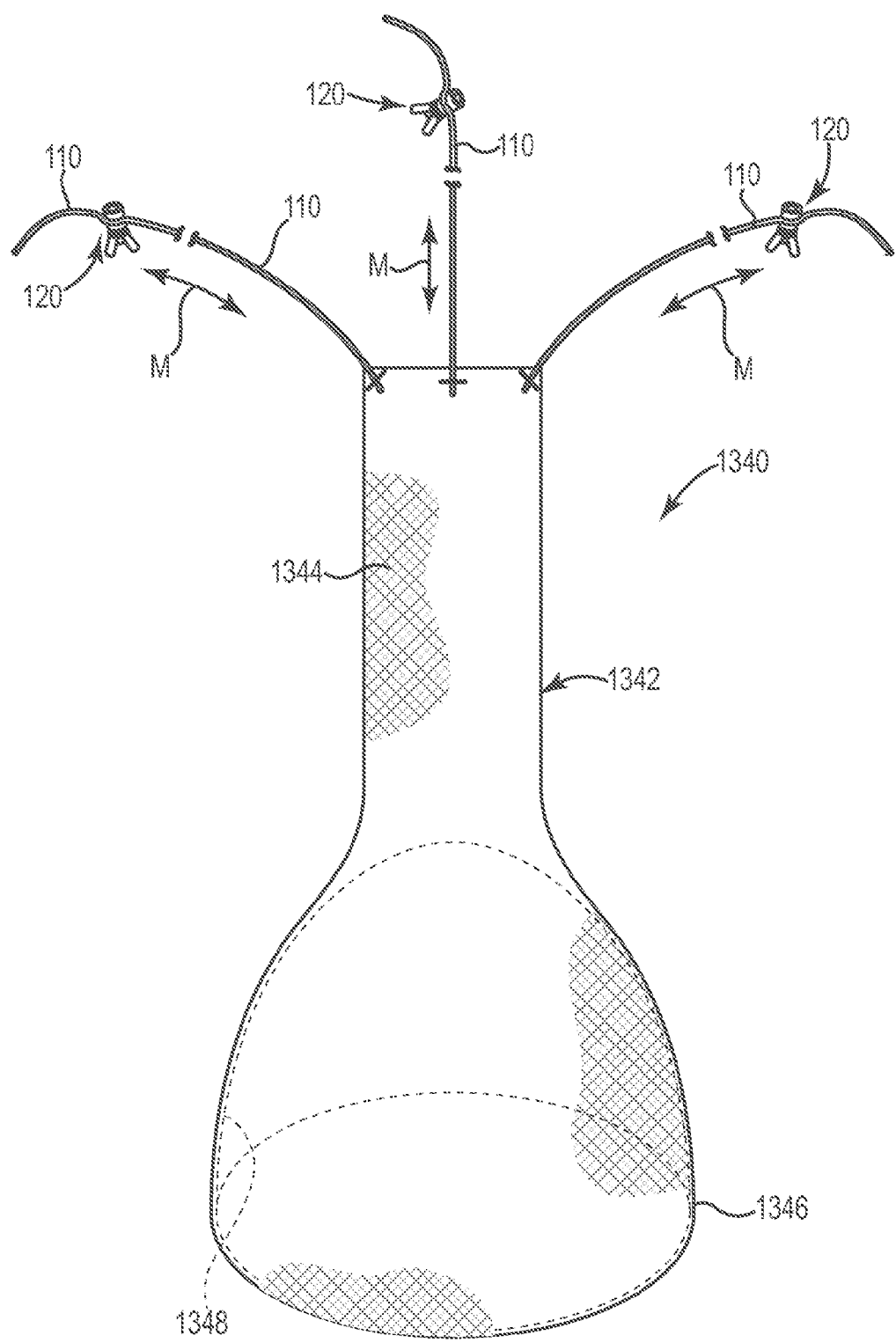
FIG. 31 is a front view of one embodiment of a sacrocolpopexy support including three adjustable connectors.

FIG. 31 is a front view of one embodiment of a sacrocolpopexy support 1340. The sacrocolpopexy support 1340 (support 1340) includes a body 1342 having a base 1344 and a leg 1346 extending the base 1344, with multiple connectors 110 and adjustable anchors 120 attached to the base 1344.

In one embodiment, the leg 1346 is fabricated as a tubular sock that defines a recess 1348 that is sized to fit over the cuff of the vagina. In one embodiment, the body 1342 is fabricated as a continuous, integrated monolithic support formed from a mesh (woven or nonwoven).

The multiple interconnecting members 110—each provided with an anchor 120—allow the symmetric placement of the support 1340, or alternatively, the asymmetric placement of the support 1340 in the treatment of vaginal vault prolapse.

Figures 32A, 32B:
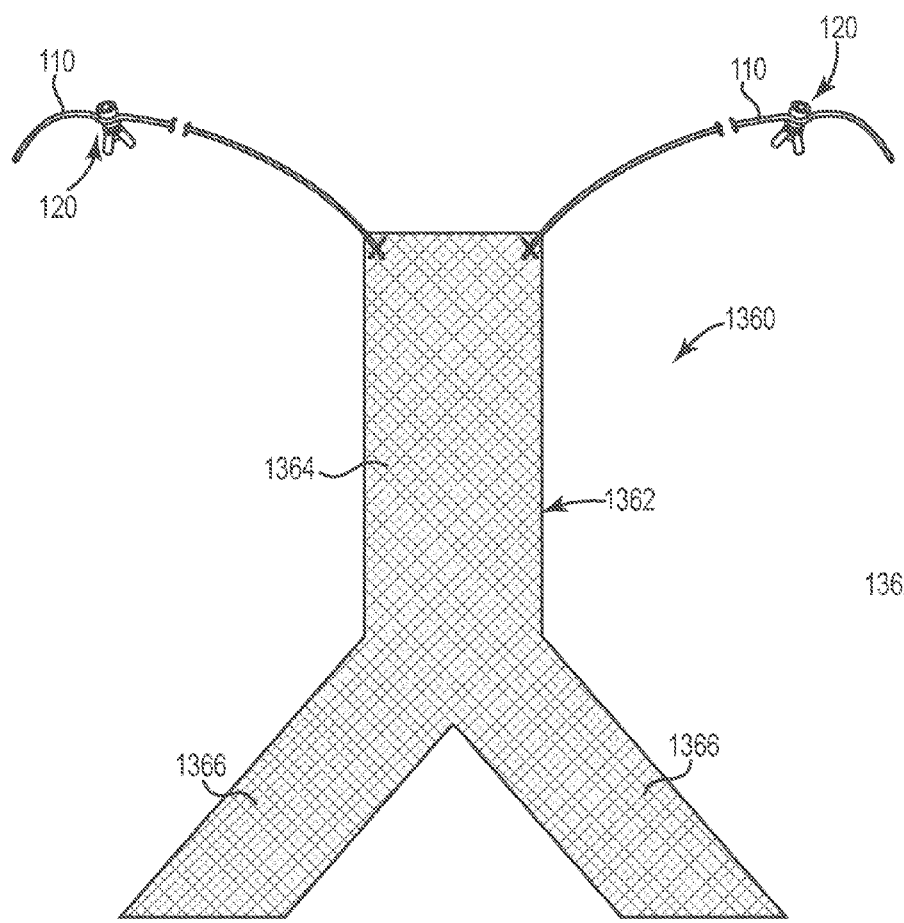
FIG. 32A is a front view and FIG. 32B is a side view of one embodiment of a planar sacrocolpopexy support.

FIG. 32A is a front view and FIG. 32B is a side view of one embodiment of a planar sacrocolpopexy support 1360. The planar sacrocolpopexy support 1360 (support 1360) includes a body 1362 having a base 1364 and legs 1366 extending from the base 1364, with the connectors 110 attached to the base 1364. In one embodiment, the body 1362 is a Y-shaped body with the base 1364 and the legs 1366 co-planar (formed in the same plane). In one embodiment, the body 1362 is stamped or cut from a planar sheet of material into the Y-shape and the connectors 110 are attached to the base 1364, which provides a low-cost manufacturing option for forming support 1360.

Figure 33:
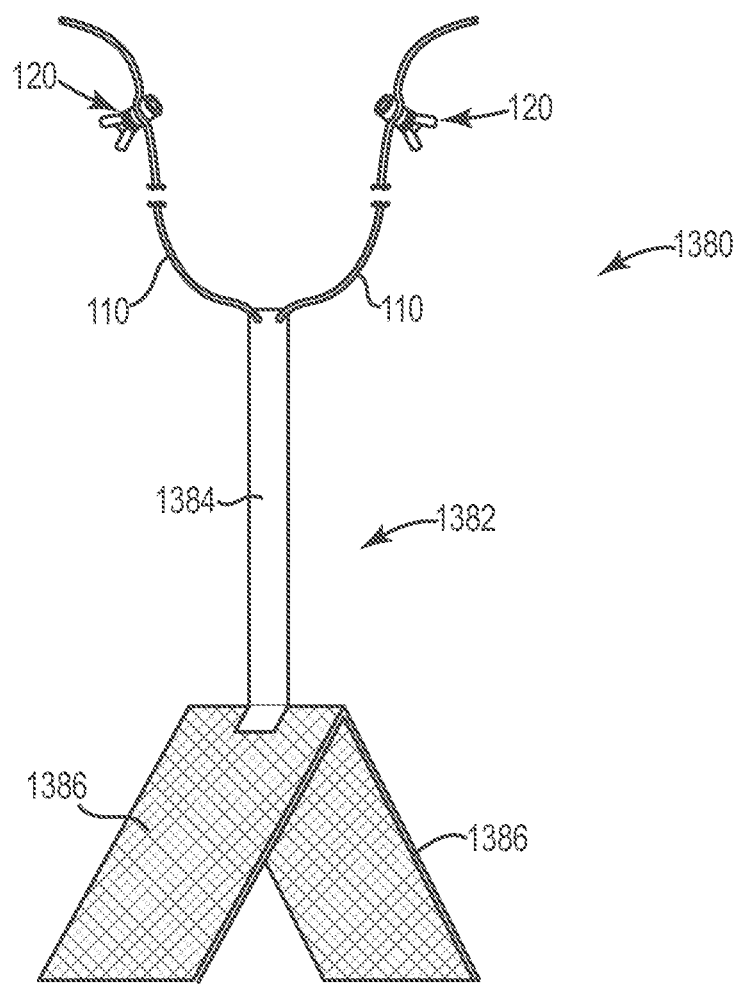
FIG. 33 is a perspective view of one embodiment of a sacrocolpopexy support.

FIG. 33 is a perspective view of one embodiment of a sacrocolpopexy support 1380. The sacrocolpopexy support 1380 (support 1380) includes a body 1382 having a base 1384 and legs 1386 extending from the base 1384, with the connectors 110 attached to the base 1384.

In one embodiment, the base 1384 is formed to have a tensile strength that is greater than the tensile strength of the legs 1386. For example, in one embodiment the base 1384 is fabricated from a robust mesh of fibers and the legs 1386 is fabricated from a softer mesh of fibers, where the diameter of the fibers in the material of the base 1384 is larger and thus stronger than the diameter (and strength) of the fibers the mesh of the legs 1386. In one embodiment, the base 1384 material is provided with a tensile strength of between about 20-50 pounds force at break and the leg 1386 material is provided with a tensile strength of between about 5-20 pounds force at break. In one embodiment, the base 1384 material is sewn or affixed to the leg 1386 material, although adhesive coupling, sonic welding, or other forms of attachment are also acceptable.

While implantable devices, tools, and methods for anatomical support have been particularly shown and described herein with reference to the accompanying specification and drawings, it will be understood however that other modifications thereto are of course possible; and all of which are intended to be within the true spirit and scope of the claimed invention. It should be appreciated that (i) components, dimensions, shapes, and other particulars of the example embodiments herein may be substituted for others that are suitable for achieving desired results, (ii) various additions or deletions may be made thereto, and (iii) features of the foregoing examples may also be made in combinations thereof. It is also to be understood in general that any suitable alternatives may be employed to provide these implantable devices, tools, and methods for anatomical support.

Lastly, choices of compositions, sizes, and strengths of various aforementioned elements, components, and steps all depend upon intended uses thereof. Accordingly, these and other various changes or modifications in form and detail may also be made, again without departing from the true spirit and scope of the invention as defined by the appended claims.

What is claimed is:

1. A sacrocolpopexy support comprising:
    a Y-shaped body having a planar base and a pair of legs extending from the planar base, where each leg in the pair of legs is sized for attachment to an exterior surface of a cuff of a vagina of a patient;
    a first interconnecting member coupled to the planar base of the Y-shaped body; and
    an adjustable anchor including a collar disposed over a body, the collar including a sidewall having a first aperture in the sidewall and a second aperture in the sidewall;
    wherein the first interconnecting member is located in the first aperture of the collar, between an inside surface of the sidewall of the collar and an outside surface of the body and circumferentially around a portion of the outside surface of the body, and in the second aperture of the collar to allow the adjustable anchor to move bi-directionally along a complete length of the first interconnecting member.

2. The sacrocolpopexy support of claim 1, wherein the planar base and the pair of legs extending from the planar base are monolithically formed.

3. The sacrocolpopexy support of claim 1, wherein each leg in the pair of legs is bifurcated away from the planar base at a non-zero acute angle.

4. The sacrocolpopexy support of claim 1, wherein each leg in the pair of legs is planar.

5. The sacrocolpopexy support of claim 1, wherein the planar base and the pair of legs extending from the planar base are co-planar.

6. The sacrocolpopexy support of claim 1, wherein the planar base is formed to have a tensile strength that is greater than a tensile strength of a leg of the pair of legs.

7. The sacrocolpopexy support of claim 1, wherein the adjustable anchor is an adjustable soft tissue anchor configured for anchoring in soft tissue of the patient.

8. The sacrocolpopexy support of claim 1, wherein the adjustable anchor includes a flange section.

9. The sacrocolpopexy support of claim 8, wherein a plurality of flanges protrudes from the flange section, with a web formed between adjacent flanges in the plurality of flanges.

10. The sacrocolpopexy support of claim 1, wherein the collar and the body exert a compressive force on the first interconnecting member generating frictional interference between the adjustable anchor and the first interconnecting member to inhibit the bi-directional movement of the adjustable anchor along the first interconnecting member unless sufficient force is applied to overcome the frictional interference.

11. The sacrocolpopexy support of claim 1, wherein the first interconnecting member is a suture.

12. The sacrocolpopexy support of claim 1, comprising a second interconnecting member coupled to the planar base of the Y-shaped body and a second adjustable anchor coupled to and moveable bi-directionally along the second interconnecting member.

13. A sacrocolpopexy support comprising:
   a Y-shaped body having a planar base and a pair of legs extending from the planar base, where each leg in the pair of legs is sized for attachment to an exterior surface of a cuff of a vagina of a patient;
   a first interconnecting member including a pulling end for a user to grasp and an end coupled to the planar base of the Y-shaped body and a length extending from the pulling end to the end coupled to the planar base; and
   an adjustable anchor including a collar disposed over a body, the collar including a sidewall having a first aperture in the sidewall and a second aperture in the sidewall;
   wherein the first interconnecting member is located in the first aperture of the collar, between an inside surface of the sidewall of the collar and an outside surface of the body and circumferentially around a portion of the outside surface of the body, and in the second aperture of the collar to allow the adjustable anchor to move bi-directionally along the length between the pulling end of the first interconnecting member and the end coupled to the planar base.

\* \* \* \* \*